United States Patent [19]

Montgomery et al.

[11] Patent Number: 5,102,873
[45] Date of Patent: Apr. 7, 1992

[54] ADENOSINE COMPOUNDS USEFUL IN THE PREVENTION AND TREATMENT OF VACCINIA VIRUS INFECTIONS

[75] Inventors: John A. Montgomery; John A. Secrist, III, both of Birmingham; Charles A. Krauth, Shelby, all of Ala.

[73] Assignee: Southern Research Institute, Birmingham, Ala.

[21] Appl. No.: 416,308

[22] Filed: Oct. 3, 1989

[51] Int. Cl.$^5$ .................... A61K 31/70; C07H 19/167; C07H 19/173

[52] U.S. Cl. ..................................... 514/46; 514/45; 536/26; 536/24

[58] Field of Search ...................... 514/45, 46; 536/24, 536/26

[56] References Cited

PUBLICATIONS

Krauth et al., "Synthesis and Antiviral Evaluation of Adenosine-N$^1$-oxide and 1-(Benzyloxy) Adenosines," in *Nucleosides, Nucleotides, and Their Biological Applications,* Oct. 4, 1988, Orange Beach, Ala., U.S.A., see p. 31, Abstract 38.

Fujii et al., "3-Methyladenine Nucleosides: Their Synthesis, Ring Opening, and Glycosidic Bond Cleavage," in *Nucleic Acids Research Symposium Series No. 8,* IRL Press Limited, London, England, 1980, pp. s17–s19.

Kaneko et al., *Chem. Abstr.,* 106: 196,740r (1987).

Fujii et al., *Chem. Abstr.,* 102: 220,260z (1985).

Shannon et al., *J. Med. Chem.,* 17, 361–363 (1974).

Krauth et al., "Synthesis and Antiviral Evaluation of Adenosine-N$^1$-oxide . . . ", *Nucleosides-Nucleotides,* 8, 915–917 (1989).

*Primary Examiner*—Johnnie R. Brown
*Assistant Examiner*—L. Eric Crane
*Attorney, Agent, or Firm*—Roylance, Abrams, Berdo & Goodman

[57] ABSTRACT

Substituted 1-(benzyloxy)adenosines and the use of substituted 1-(benzyloxy)adenosines and adenosine-N$^1$-oxides in the prevention and treatment of vaccinia virus infections are disclosed.

42 Claims, No Drawings

ADENOSINE COMPOUNDS USEFUL IN THE PREVENTION AND TREATMENT OF VACCINIA VIRUS INFECTIONS

This invention was made with government support awarded by the U.S. Army Medical Research Institute of Infectious Diseases under Contract No. DAMD17-86-C-6011. The government has certain rights in this invention.

BACKGROUND OF THE INVENTION

This invention relates to certain novel substituted 1-(benzyloxy)adenosines and to the use of substituted 1-(benzyloxy)adenosines and adenosine-$N^1$-oxides in the prevention and treatment of vaccinia virus infections.

Vaccinia virus has been used historically to prevent smallpox infections. Although the use of vaccinia virus for this purpose is usually considered to be safe, significant complications to the vaccine can occur. These complications include disseminated vaccinia (1 in 25,000 vaccinees) and vaccinia gangrenosum (1 in approximately 20,000 individuals). These complications are rarely life threatening; however, they are of a morbid nature being debilitating and resulting in a loss of work time.

Currently, genetically engineered strains of vaccinia virus are under evaluation as vectors for delivering antigens to prevent other viral infections. The increased use of vaccinia virus strains due to their usefulness as vectors could be expected to increase the incidence of vaccinia virus infections. Therefore, it would be desirable to have an antiviral drug useful for the prevention and treatment of complications associated with the administration of vaccinia.

Shannon et al, J. Med. Chem. 17, 361–363 discloses the compounds adenosine 1-oxide, 1-methyladenosine, 2-methyladenosine, N-hydroxyadenosine, 2'-deoxyadenosine 1-oxide, 1-benzyloxyadenosine, 1-(2-methylbenzyloxy)adenosine fluoroborate, 1-(3-methylbenzyloxy)adenosine hydrobromide, 1-(4-methylbenzyloxy)adenosine hydrobromide, 1-(3-fluorobenzyloxy)adenosine fluoroborate, 1-(4- fluorobenzyloxy)adenosine fluoroborate, and 1-(4-nitrobenzyloxy) adenosine fluoroborate, and reports their in vitro antiviral activity against a number of animal viruses, including vaccinia virus (strain Lederle chorioallantoic).

SUMMARY OF THE INVENTION

It has now been found that certain adenosine-$N^1$-oxides and substituted 1-(benzyloxy)adenosines are potent inhibitors of vaccinia virus in an animal model, and would be useful in the treatment of vaccinia virus disease such as complications arising from the use of the vaccinia virus as a vaccine or as a vector. According to the method of this invention, there is administered to a host animal, including man, afflicted with a viral infection caused by vaccinia virus or exposed to vaccinia virus by the administration of the virus as a vaccine or vector, and in need of preventative treatment a therapeutically or prophylactically effective amount of a compound selected from the group of the following adenosine $N^1$ oxides and substituted 1-(benzyloxy) adenosines

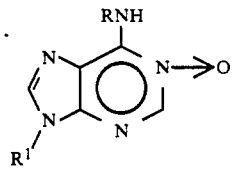

where R is hydrogen or methyl and $R^1$ is ribosyl or 2'-deoxyribosyl and

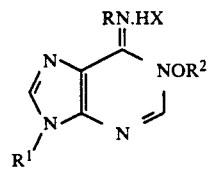

where R is hydrogen or methyl, $R^1$ is ribosyl or 2'-deoxyribosyl and $R^2$ is alkyl or substituted arylalkyl.

According to another aspect of this invention, there are provided certain novel substituted 1-(benzyloxy) adenosines having useful antiviral activities and represented by the formula

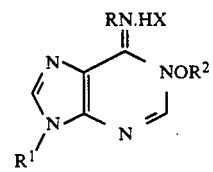

where
X is perchlorate, hydrogen or fluoroborate,
R is hydrogen or methyl
$R^1$ is ribosyl or 2'-deoxyribosyl, and
$R^2$ is a member selected from the group consisting of the following substituted arylalkyl groups:

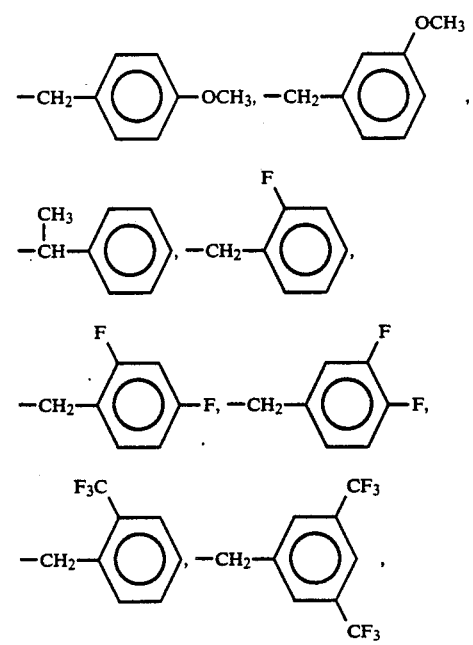

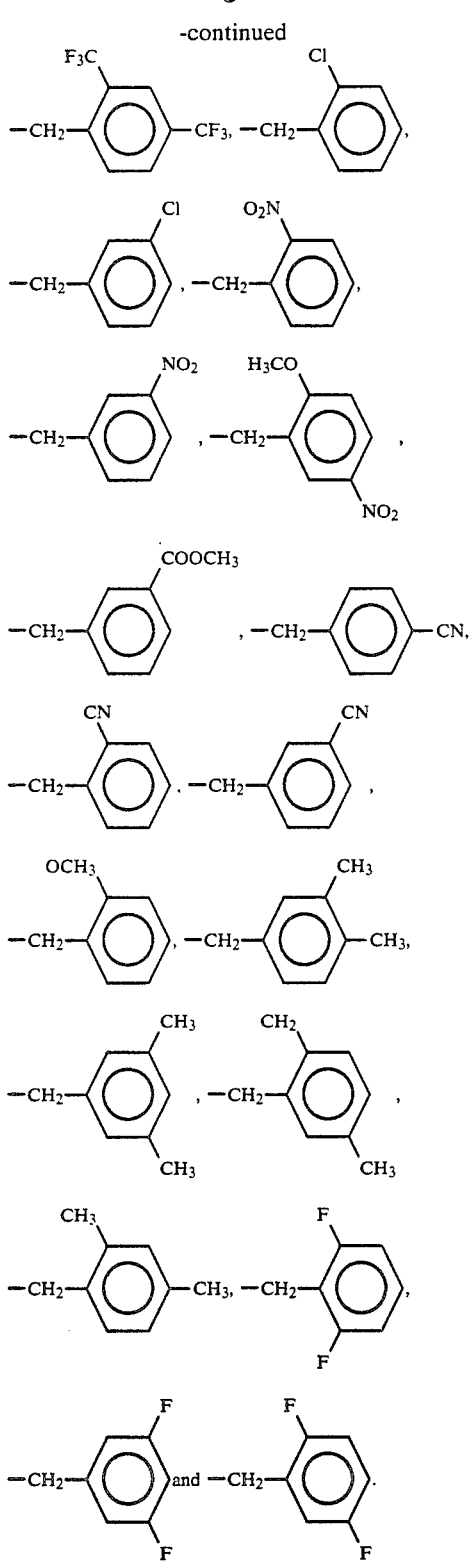

DETAILED DESCRIPTION OF THE INVENTION

Adenosine-N$^1$-oxide is synthesized by reacting adenosine with m-chloroperoxybenzoic acid in methanol. 2'-Deoxyadenosine-N$^1$-oxide and 6-methylamino-9-β-D-ribofuranosylpurine-N$^1$-oxide were prepared in a similar manner.

1-(Substituted benzyloxy) adenosines are prepared by reacting an adenosine-N$^1$-oxide with the appropriate benzyl bromide. Perchlorate salts are prepared by the addition of ammonium perchlorate.

The following examples illustrate the preparation of the compounds described above.

All solvents and materials were reagent grade and were either used as received or purified as required. $^1$H NMR and $^{13}$C NMR spectra were run with a Nicolet NMC NT-300 NB spectrometer operating at 300.65 MHz with tetramethylsilane as an internal reference. Chemical shifts (δ) for multiplets were measured from the appropriate centers. The mass spectral data were obtained from a Varian MAT 311A mass spectrometer in fast atom bombardment (FAB) or electron-impact (EI) mode (direct probe temperature 20° C.), as indicated. Infrared data were obtained with a Nicolet 10-MX spectrometer. In most cases only strong or medium peaks in the 1800-600 cm$^{-1}$ range were reported. UV absorption spectra were determined in the appropriate [pH 1 (0.1N HCl), pH 7 buffer, and pH 13 (0.1N NaOH)] solutions with a Cary 17 spectrophotometer or a Perkin Elmer Model Lambda 9 UV/VIA/NIR spectrophotometer. Melting point data was obtained with a Mel-Temp Capillary Melting point apparatus, and all melting points were uncorrected. Elemental analysis data were obtained either from Atlantic Microlab of Atlanta, Ga. or The Southern Research Institute of Birmingham, Ala.

In the following examples, MeOH is methanol, EtOH is ethanol and MCPBA is m-chloroperoxybenzoic acid.

EXAMPLE 1

Adenosine-N$^1$-oxide (1a). In a 1-L round-bottomed flask protected with a calcium sulfate drying tube was placed a 5.0 g (18.7 mmol) of adenosine and 500 mL of methanol. The mixture was stirred at room temperature and 4.85 g (22.5 mmol) of m-chloroperoxybenzoic acid (MCPBA) was added in 7-10 portions over 2 hours. If thin-layer chromatography after 15-20 hours of stirring indicates the presence of starting material an additional 0.5 g (2.9 mmol) of MCPBA should be added and the reaction stirred an additional 4 hours. If the TLC continues to show starting material another portion of MCPBA must be added and the stirring continued overnight. After the TLC showed little or no starting material left the reaction mixture was poured slowly in 2 L of ethyl acetate with good stirring. After having been stirred 2 hours, the product was collected, washed with ethyl acetate, and dried in vacuo over phosphorus pentoxide: yield 4.6 g. Melting point and elemental analysis data are set forth in Table I.

UV λ$_{max}$ 212 nm (ε28,300), 257 (12,500), 265 (sh) at pH 1; 232 (41,900), 262 (8,300), 295 (2,400) at pH 7; 231 (24,900), 267 (8,800), 275 (sh), 307 (4,700) at pH 13; 235 (41,400), 263 (7,700), 304 (2,250) in EtOH; MS (FABMS) m/e 284 (M+1); IR 1670, 1500, 1225, 1210, 1135 sh, 1125, 1085, 1060, 640 cm$^{-1}$; $^1$H NMR (Me$_2$SO-d$_6$) δ 3.57, 3.69 (2 m, 2, J$_{5'a,5'b}$=12.0, CH$_2$.5'), 3.96 (apparent q, 1, J$_{4,5'b}$=4.0 Hz, J$_{4',5'a}$=4.1 Hz, H-4'), 4.16 (apparent q, 1, J$_{3', 4'}$=3.7 Hz, H-3'), 4.56 (apparent q, 1, J$_{2', 3'}$=5.0 Hz, H-2'), 5.09 (apparent t, 1, 5'-OH), 5.28 (apparent d, 1, 3'-OH), 5.64 (apparent d, 1, 2'-OH), 5.89 (d, 1, H-1'), 8.55 (s, 1, H-2), 8.64 (s, 1, H-8).

EXAMPLE 2

2'-Deoxyadenosine-N$^1$-oxide (1b) was prepared using the procedure set forth in Example 1. Table 1 sets forth the amount of reactant used. The same ratio of reactants and solvents was maintained. Melting point and elemental analysis data are set forth in Table 1. UV, IR, $^1$H NMR, $^{13}$C NMR and mass spectrometer data are set forth herein.

UV $\lambda_{max}$ 258 nm (12,520) at pH 1; 261 (8,490) at pH 7; 268 (8,600) at pH 13; MS (FAB) m/e 268 (M+1); IR 1680, 1499, 1380, 1233, 1213, 1091, 1075, 1070, 1025 cm$^{-1}$; $^1$H NMR (Me$_2$SO-d$_6$) δ 2.32 (m, 1, $J_{2'a,3'}$=3.6 Hz, $J_{1',2'a}$=6.2 Hz, H-2'a), 2.70 (m, 1, $J_{2',3'}$=5.9 Hz, $J_{1',2'}$=7.2 Hz, $J_{2'a,2'}$=13.3 Hz, H-2'b), 3.52, 3.60 (2 m, 2, $J_{5'a,5'b}$=11.8 Hz, CH$_2$-5'), 3.87 (apparent q, 1, $J_{4',5'a}$=$J_{4',5'b}$=4.7 Hz, H-4'), 4.41 (apparent q, 1, $J_{3',4'}$=2.7 Hz, $J_{2'a,3'}$=3.6 Hz, $J_{2'b,3'}$=5.9 Hz, H-3'), 4.98 (apparent t, 1, $J_{5',5'-OH}$=5.0 Hz, 5'-OH), 5.38 (apparent d, 1, $J_{3',3'-OH}$= 3.8 Hz, 3'-OH), 6.33 (apparent t, 1, $J_{1',2'a}$=6.2 Hz, $J_{1',2'b}$=7.2 Hz, H-1'), 8.51 (s, 1, H-2), 8.63 (s, 1, H-8). Anal. Calcd for C$_{10}$H$_{13}$N$_5$O$_4$·0.40H$_2$O: C, 43.76; H, 5.07; N, 25.52. Found: C, 43.83; H, 5.06; N, 25.28.

EXAMPLE 3

6-Methylamino-9-β-D-ribofuranosylpurine-N$^1$-oxide (1c).$^{1-3}$was prepared using the procedure set forth in Example 1. Table 1 sets forth the amount of reactant used. The same ratio of reactants and solvents was maintained. Melting point and elemental analysis data are set forth in Table 1. UV, IR, $^1$H NMR, $^{13}$C NMR and mass spectrometer data are set forth herein.

UV $\lambda_{max}$ 215 nm (25,800), 262 nm (13,900) at pH 1; 235 (37,900), 270 (9,800) at pH 7; 235 (38,000), 271 (9,500); MS (FAB) m/e 298 (M+1); IR 1656, 1580, 1500, 1425, 1215, 1090 (broad), 1050, 1025 cm$^{-1}$; $^1$H NMR (Me$_2$SO-d$_6$) δ 3.45 (apparent d, 3, NCH$_3$), 3.54, 3.66 (2 m, 2, $J_{4',5'a}$=4.0 Hz, $J_{4',5'b}$=3.9 Hz, $J_{5'a,5'b}$=12.0 Hz, CH$_2$-5'), 3.93 (apparent q, 1, H-4'), 4.16 (apparent q, 1, $J_{3',4'}$=3.8 Hz, H-3'), 4.51 (apparent q, 1, $J_{2',3'}$=5.0 Hz, H-2'), 5.07 (t, 1, $J_{5',5'-OH}$=5.5 Hz, OH-5'), 5.24 (d, 1, $J_{3',3'-OH}$=5.1 Hz, OH-3'), 5.59 (d, 1, $J_{2',2'-OH}$=5.9 Hz, OH-2'), 5.88 (d, 1, $J_{1',2'}$=5.5 Hz, H-1'), 8.39 (br d, 1, CH$_3$N-H), 8.55 (s, 1, H-2), 8.62 (s, 1, H-8).

EXAMPLE 4

General procedure for the preparation of 1-(Substituted benzyloxy)adenosines, perchloric acid salts.

In a 100-mL round-bottomed flask equipped with a magnetic stirrer and a calcium sulfate drying tube was placed 2.5 g (8.83 mmol) of adenosine-N$^1$-oxide (1), 50 mL of molecular sieve (4A) dried N,N-dimethyl acetamide (DMAC), and 26.5 mmol of the appropriate benzyl bromide was added to the well-stirred suspension. The benzyl bromide used depends upon the product desired. For example, to make 1-(3-methylbenzyloxy)adenosine, the benzyl bromide use is 3-methylbenzyl bromide. The mixture was stirred for 2 hours after complete solution was achieved. The reaction mixture was poured into 300–500 mL of anhydrous ether with slight swirling. After the product stuck to the walls of the flask the supernatant was decanted. The gummy residue was washed with 400 mL of ether, decanted, again covered with 400 mL of ether, and ground to a powder. The powder was allowed to settle, the ether was decanted and the residue was dried in a stream of argon. The residue was dissolved in 25 mL of H$_2$O and added with stirring to a warm solution of 5 g (42.6 mmol) of ammonium perchlorate dissolved in 25 mL of H$_2$O. The product crystallized upon scratching and chilling. One recrystallization from H$_2$O and drying at either 56° C. or 78° C. for 16 hours over phosphorus pentoxide usually yielded an analytical sample (see Table 2).

EXAMPLE 5

1-(3-Methylbenzyloxy)adenosine, perchloric acid salt (2a) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV δ$_{max}$ 258 nm (12,400) at pH 1; 258 (12,400) at pH 7; 257 (12,550) at pH 13; MS (FAB) m/e 388 (M+1); IR 1690, 1224, 1088 broad, 623 cm$^{-1}$, $^1$H NMR (Me$_2$SO-d$_6$) δ 2.35 (s, 3, CH$_3$), 3.58, 3.69 (2 m, 2, $J_{4',5'a}$=3.9 Hz, $J_{4',5'b}$=4.0 Hz, $J_{5'b,5'a}$=12.0 Hz, CH$_2$-5'), 4.01 (apparent q, 1, H-4'), 4.15 (apparent t, 1, $J_{3',4'}$ 3.8 Hz, H-3'), 4.48 (apparent t, 1, $J_{2',3'}$=4.9 Hz, H-2'), 5.00–5.16 (br s, 1, 5'-OH), 5.22–5.43 (m, 1, 3'-OH), 5.36 (s, 2, O-CH Ar), 5.50–5.62 (br s, 1, 2'-OH), 5.93 (d, 1, $J_{1',2'}$=5.4 Hz, H-1'), 7.25–7.50 (m, 4, H-Ar), 8.81 (s, 1, H-8), 8.95 (s, 1, H-2), 9.72 (br s, 1, H-N$^⊕$H$_2$), 10.40 (br s, 2, H-N$^⊕$H$_2$).

EXAMPLE 6

1-(4-Methylbenzyloxy)adenosine, perchloric acid salt (2b) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 259 nm (12,900) at pH 1; 259 (12,600) at pH 7; 258 (12,510) at pH 13; MS (FAB) m/e 388 (M+1); IR 1679, 1505, 1425, 1220, 1100 (broad), 855, 623 cm$^{-1}$; $^1$H NMR (Me$_2$SO-d$_6$) δ 2.34 (s, 3, H-ArCH$_3$), 3.59, 3.67 (2 m, 2, $J_{4',5'a}$=3.8 Hz, $J_{4',5'b}$=4.0 Hz, $J_{5'a,5'b}$=12.0 Hz, CH$_2$-5'), 4.00 (apparent q, 1, H-4'), 4.16 (apparent t, 1, $J_{3',4'}$=3.9 Hz, H-3'), 4.49 (apparent t, 1, $J_{2',3'}$=4.8 Hz, H-2'), 5.09, 5.32, 5.59 (3 br s, 3, 5', 3', 2'-OH), 5.37 (s, 2, OCH$_2$Ar), 5.94 (d, 1, $J_{1',2'}$=5.4 Hz, H-1'), 7.26 (d, 2, Ar-H-3,5), 7.54 (d, 2, Ar-H-2,6), 8.81 (s, 1, H-8), 8.92 (s, 1, H-2), 9.73, 10.39 (2 br s, 2, H-N$^⊕$H$_2$).

EXAMPLE 7

1-(2-Methylbenzyloxy)adenosine, perchloric acid salt (2c) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 259 nm (13,420) at pH 1; 259 (13,260) at pH 7; 258 (13,210) at pH 13; MS (FAB) m/e 388 (M +1); IR 1687, 1510, 1415, 1227, 1127, 1083 (broad), 916, 880, 767, 690, 623 cm$^{-1}$; $^1$H NMR (Me$_2$SO-d$_6$) δ 2.47 (s, 3, CH$_3$), 3.57, 3.68 (2 m, 2, $J_{4',5'a}$=3.9 Hz, $J_{4',5'b}$32 4.0 Hz, $J_{5'a,5'b}$=12.0 Hz, CH$_2$-5'), 3.99 (apparent q, 1, H-4'), 4.15 (apparent t, 1, $J_{3',4'}$=3.8 Hz, H-3'), 4.47 (br s, 1, $J_{2',3'}$=4.9 Hz, H-2'), 5.08 (br s, 1, 5'-OH), 5.32 (br s, 1, 3'-OH), 5.46 (s, 2, OCH$_2$Ar), 5.60 (br s, 1, 2'-OH), 5.92 (d, 1, $J_{1',2'}$=5.4 Hz, H-1'), 7.35 (m, 4, H-Ar), 8.61 (s, 1, H-2), 8.83 (s, 1, H-8), 9.79 (br s, 1, H-N$^⊕$H$_2$), 10.48 (br s, 1, H-N$^⊕$CH$_2$); $^{13}$C NMR (Me$_2$SO-d$_6$) δ 18.64 (CH$_3$), 60.83 (C-5'), 69.92 (C-3'), 74.46 (C-2'), 79.56 (C-OCH$_2$Ar), 85.83 (C-4'), 87.74 (C-1'), 119.84 (C-5), 125.84 (Ar-C3), 129.93 (Ar-C6), 130.45 (Ar-C4), 131.34 (Ar-C2), 138.13 (Ar-C1), 142.84 (C-8), 144.40 (C-2), 145.17 (C-4), 148.32 (C-6).

EXAMPLE 8

1-(4-Methoxybenzyloxy)adenosine, perchloric acid salt (2d) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 258 nm (13,900) at pH 1; 259 (12,100) at pH 7; 259 (11,400) at pH 13; MS (FAB) m/e 404 (M+1); IR 1684, 1610, 1516, 1252, 1229, 1180, 1100 broad, 623 cm$^{-1}$; $^1$H NMR (Me$_2$SO-d$_6$) δ 3.58, 3.70 (2 m, 2, CH$_2$-5'), 3.79 (s, 3, OCH$_3$), 3.99 (apparent q, 1, H-4'), 4.16 (apparent q, 1, H-3'), 4.49 (apparent q, 1, H-2'), 5.09 (apparent t, 1 OH-5'), 5.33 (apparent d, 1 OH-3'), 5.35 (s, 2, OCH$_2$Ar), 5.60 (d, 1, 2, Ar-H-2,6), 8.80 (s, 1, H-8), 8.87 ( s, 1, H-2), 10.02 (br OH-2'), 5.93 (d, 1, H-1'), 6.99 (d, 2, Ar-H-3,5), 7.69 (d, 2, Ar-H-2,6), 8.80 (s, 1, H-8), 8.87 (s, 1, H-2), 10.02 (br s, 2, H-N$^\oplus$H$_2$).

EXAMPLE 9

1-(3-Methoxybenzyloxy)adenosine, perchloric acid salt (2e) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 260 nm (13,200) at pH 1; 260 (12,700) at pH 7; 258 (13,100) at ph 13; MS (FAB) m/e 404 (M+1); IR 1683, 1605, 1510, 1495 1435 1270 1100 (broad), 623 cm$^{-1}$; $^1$H NMR (Me$_2$SO-d$_6$) δ 3.56, 3.68 (2 m, 2, CH$_2$-5'), 3.78 (s, 3, OCH$_3$), 3.98 (apparent q, 1, H-4'), 4.14 (apparent q, 1, H-3'), 4.47 (apparent q, 1, H-2'), 5.07 (apparent t, 1 OH-5'), 5.31 (apparent d, 1 OH-3'), 5.36 (s, 2, OCH$_2$Ar), 5.59 (apparent d, 1, OH-2'), 5.92 (d, 1, H-1'), 7.03 (m, 1, Ar-H-4), 7.19 (d, 1, Ar-H-6), 7.28 (apparent t, 1, Ar-H-2), 7.37 (t, 1, Ar-H-5), 8.76 (s, 1, H-8), 8.88 (s, 1, H-2), 9.95 (br s, 2, H-N$^\oplus$H$_2$).

EXAMPLE 10

1-(1-Phenylethyloxy)adenosine, perchloric acid salt (2f) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 259 nm (12,400) at pH 1; 259 (12,500) at pH 7; 258 (12,900) at pH 13; MS (FAB) m/e 388 (M+1); IR 1691, 1510, 1430, 1400, 1325, 1225, 1100 (broad), 875, 720, 705, 635, 624 cm$^{-1}$; $^1$H NMR (Me$_2$SO-d$_6$) δ 1.80 (d, 3, CH$_3$), 3.55, 3.65 (2 m, 2, CH$_2$-5'), 3.95 (apparent q, 1, H-4'), 4.12 (apparent t, 1, H-2'), 4.43 (apparent t, 1, H-2'), 5.07, 5.31, 5.68 (3 apparent s, 3, OH-5', 3'-2'), 5.71 (apparent q, 1, OCHAr), 5.90 (m, 1, H-1'), 7.42, 7.59 (2 m 5, Ar-H), 8.77 (apparent t, 2, H-8,2), 9.53, 10.32 (2 br s, 2, H-N$^\oplus$H$_2$). $^{13}$C NMR (Me$_2$SO-d$_6$) δ 18.61 (C-CH$_3$), 60.80 (C-5'), 69.88 (C-3'), 74.39 (C-2'), 85.83 (C-4'), 87.65 (C-1'), 88.60 (C-OCHAr), 118.97 (C-5), 128.49, 128.54 (Ar-C-2,3,5,6), 129.85 (Ar-C-4), 136.05 (Ar-C-1), 142.83 (C-8), 144.72 (C-2), 144.89 (C-4), 148.61 (C-6).

EXAMPLE 11

1-(2-Fluorobenzyloxy)adenosine, perchloric acid salt (2g) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 259 nm (13,400) at pH 1; 259 (13,100) at pH 7; 257 (12,500) at pH 13; MS (FAB) m/e 392 (M+1); IR 1686, 1515, 1415, 1227, 1100 (broad), 770, 622 cm$^{-1}$; $^1$H NMR (Me$_2$SO-d$_6$) δ 3.58, 3.69 (2 m, 2, CH$_2$-5'), 3.99 (apparent q, H-4'), 4.15 (apparent t, 1, H-3'), 4.48 (apparent s, 1, H-2'), 5.09, 5.33 (2 br s, 2, OH-5'3'), 5.52 (s, 2, OCH$_2$Ar), 5.60 (br s, 1, OH-2'), 5.94 (d, 1, H-1'), 7.30, 7.56, 7.69 (3 m, 4, Ar-H), 8.79 (s, 1, H-2), 8.82 (s, 1, H-8), 9.78, 10.44 (2 br s, 2, H-N$^\oplus$H$_2$).

EXAMPLE 12

1-(3-Fluorobenzyloxy)adenosine, perchloric acid salt (2h) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 259 nm (13,700) at pH 1; 259 (13,700) at pH 7; 258 (13,100) at pH 13; MS (FAB) m/e 392 (M+1); IR 1684, 1507, 1100 (broad), 623 cm$^{-1}$; $^1$H NMR (Me$_2$SO-d$_6$) δ 3.59, 3.69 (2 m, 2, CH$_2$-5'), 4.00 (apparent q, 1, H-4'), 4.16 (apparent t, 1, H-3'), 4.49 (apparent t, 1, H-2'), 5.43 (s, 2, OCH$_2$Ar), 5.97 (d, 1, H-1'), 7.34, 7.52, 7.63 (3 m, 4, Ar-H), 8.83 (s, 1, H-8), 9.05 (s, 1, H-2), 9.78, 10.44 (2 br s, 2, H-N$^\oplus$H$_2$).

EXAMPLE 13

1-(4-Fluorobenzyloxy)adenosine, perchloric acid salt (2i) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 258 nm (12,500) at pH 1; 258 (12,300) at pH 7; 257 (12,400) at pH 13; MS (FAB) m/e 392 (M+1); IR 1690, 1511, 1226, 1100 broad, 874, 855, 623 cm$^{-1}$; $^1$H NMR (Me$_2$SO-d$_6$) δ 3.59, 3.70 (2 m, 2, $J_{4',5'a}$=3.9 Hz, $J_{4',5'b}$=4.0 Hz, $J_{5'a,5'b}$=12.0 Hz, CH$_2$-5'), 4.00 (apparent q, 1, H-4'), 4.17 (apparent t, 1, $J_{3',4'}$=3.8 Hz, H-3'), 4.50 (apparent t, 1, $J_{2',3'}$=4.9 Hz, H-2'), 5.09 (br s, 1, 5'-OH), 5.32 (br s, 1, 3'-OH), 5.41 (s, 2, O-CH$_2$Ar), 5.59 (br d, 1, 2'-OH), 5.95 (d, 1, $J_{1',2'}$=5.4 Hz, H-1'), 7.31 (t, 2, $J_{H,F}$=8.8 Hz, H-3",5"), 7.75 (m, 2, $J_{H,F}$=5.6 Hz, H-2",6"), 8.82 (s, 1, H-8), 9.00 (s, 1, H-2), 9.75 (br s, 1, H-N$^\oplus$H$_2$), 10.39 (br s, 1, H-N$^\oplus$H$_2$).

EXAMPLE 14

1-(2,4-Difluorobenzyloxy)adenosine, perchloric acid salt (2j) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 259 nm (13,500) at pH 1; 259 (13,300) at pH 7; 257 (13,000) at pH 13; MS (FAB) m/e 410 (M +1); IR 1690, 1620, 1508, 1100 (broad), and 624 cm$^{-1}$; $^1$H NMR (Me$_2$SO-d$_6$) δ 3.58, 3.70 (2 m, 2, $J_{4',5'a}$=3.7 Hz, $J_{4',5'b}$=4.0 Hz, $J_{5'a,5'b}$=12.1 Hz, CH$_2$-5'), 3.99 (apparent q, 1, H-4'), 4.16 (apparent s, 1, $J_{3',4'}$=3.9 Hz, H-3'), 4.48 (apparent q, 1, $J_{2',3'}$=4.9 Hz, H-2'), 5.09, 5.33 (2 apparent s, 2, OH-5',3'), 5.47 (s, 2, OCH$_2$Ar), 5.60 (apparent d, 1, OH-2'), 5.94 (d, 1, $J_{1',2'}$=5.3 Hz, H-1'), 7.22, 7.39 (2 m 2, Ar-H-3,5), 7.76 (q, 1, Ar-H-6), 8.81 (s, 2, H-8,2), 9.79, 10.44 (2 br s, 2, H-N$^\oplus$H$_2$). $^{13}$C NMR (Me$_2$SO-d$_6$) δ 60.86 (C-5'), 69.95 (C-3'), 74.36 (C-OCH$_2$Ar), 74.48 (C-2'), 85.89 (C-4'), 87.73 (C-1'), 104.24 (Ar-C-3), 111.85 (Ar-C-5), 117.00 (Ar-C-1), 119.39 (C-5), 134.60 (Ar-C-

6), 142.87 (C-8), 144.55 (C-2), 145.25 (C-4), 148.41 (C-6), 161.55, 163.47 (Ar-C-2,4).

EXAMPLE 15

1-(3,4-Difluorobenzyloxy)adenosine, perchloric acid salt (2k) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 259 nm (13,000) at PH 1; 259 (13,400) at pH 7; 258 (12,900) at pH 13; MS (FAB) m/e 410 (M+1); IR 1687, 1522, 1440, 1294, 1100 (broad), and 624 cm$^{-1}$; $^1$H NMR (Me$_2$SO-d$_6$) δ 3.59, 3.69 (2 m, 2, J$_{4',5'a}$=3.9 Hz, J$_{4',5'b}$=3.7 Hz, J$_{5'a,5'b}$=12.1 Hz, CH$_2$-5'), 4.00 (apparent q, 1, H-4'), 4.17 (apparent t, 1, J$_{3',4'}$=3.9 Hz, H-3'), 4.50 (br s, 1, J$_{2',3'}$=4.9 Hz, H-2'), 5.10, 5.35, 5.60 (3 br s, 49 3, OH-5',3',2'), 5.38 (s, 2, OCH$_2$Ar), 5.95 ( d, 1, J$_{1',2'}$= 5.3 Hz, H-1'), 7.55, 7.88 (2 m 3, Ar-H-2,5,6), 8.82 (s, 1, H-8), 9.03 (s, 1, H-2), 9.76, 10.44 (2 br s, 2, H-N⊕CH$_2$).

EXAMPLE 16

1-(2-Trifluoromethylbenzyloxy)adenosine, perchloric acid salt (2l) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 258 nm (13,100) at pH 1; 258 (12,900) at pH 7; 257 (12,700) at pH 13; MS (FAB) m/e 442 (M+1); IR 1682, 1317, 1177, 1108 (broad), 778, 624 cm$^{-1}$; $^1$H NMR (Me$_2$SO-d$_6$) δ3.58, 3.68 (2 m, 2, J$_{4',5'a}$=J$_{4',5'b}$=3.9 Hz, J$_{5'a,5'b}$=32 12.1 Hz, CH$_2$-5'), 4.00 (apparent q, 1, H-4'), 4.17 (apparent t, 1, J$_{3',4'}$=3.9 Hz, H-3'), 4.49 (apparent t, 1, J$_{2',3'}$=4.9 Hz, H-2'), 5.09 (br s, 1, 5'-OH), 5.32 (br s, 1, 3'-OH), 5.60 (br s, 1, 2'-OH), 5.61 (s, 2, O-CH$_2$Ar), 5.94 (d, 1, J$_{1',2'}$=5.3 Hz, H-1'), 7.80 (m 4, H-Ar), 8.68 (s, 1, H-2), 8.83 (s, 1, H-8), 9.81, 10.47 (2 br s, 2, H-NCH$_2$).

EXAMPLE 17

1-[3,5-Bis(trifluoromethyl)benzyloxy]adenosine, perchloric acid salt (2m) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 259 nm (12,600) at pH 1; 259 (12,280) at pH 7; 257 (12,100) at pH 13; MS (FAB) m/e 510 (M+1); IR 1684, 1366, 1282, 1129 (broad), 684, and 624 cm$^{-1}$; $^1$H NMR (Me$_2$SO-d$_6$)δ3.61, 3.68 (2 m, 2, J$_{4',5'a}$=3.8 Hz, J$_{4',5'b}$=3.9 Hz, J$_{5'a,5'b}$=11.9 Hz, CH$_2$-5'), 4.01 (apparent q, 1, H-4'), 4.18 (apparent t, 1, J$_{3',4'}$=3.8 Hz, H-3'), 4.52 (apparent t, 1, J$_{2',3'}$=4.9 Hz, H-2'), 5.08 (br s, 1, 5'-OH), 5.34 (br s, 1, 3'-OH), 5.59 (br s, 1, 2'-OH), 5.56 (s, 2, OCH$_2$Ar), 5.98 (apparent d, 1, J$_{1',2'}$=5.41 Hz, H-1'), 8.26 (s, 1, Ar-H-4), 8.52 (s, 1, Ar-H-6), 8.84 (s, 1, H-8), 9.30 (s, 1, H-2), 9.84, 10.51 (2 br s, 2, H-N⊕CH$_2$). $^{13}$C NMR (Me$_2$SO-d$_6$) δ 61.02 (C-5'), 70.15 (C-3'), 74.62 (C-2'), 79.74 (C-OCH$_2$Ar), 86.08 (C-4'), 87.96 (C-1'), 119.55 (C-5), 123.21 (Ar-C-4), 123.23 (2 C-CF$_3$), 130.35 (Ar-C-3,5), 131.74 (Ar-C-2,6), 135.37 (Ar-C-1), 143.04 (C-8), 145.14 (C-2), 145.41 (C-4), 148.39 (C-6).

EXAMPLE 18

1-[2,4-Bis(trifluoromethyl)benzyloxy]adenosine, perchloric acid salt (2n) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 259 nm (13,240) at pH 1; 259 (12,710) at pH 7; 257 (12,090) at pH 13; MS (FAB) m/e 510 (M+1); IR 1684, 1348, 1304, 1281, 1123 (broad), 624 cm$^{-1}$; $^1$H NMR (Me$_2$SO-d$_6$) δ 3.60, 3.69 (2 m, 2, J$_{4',5'a}$=3.8 Hz, J$_{4',5'b}$=3.6 Hz, J$_{5'a,5'b}$=12.3 Hz, CH$_2$-5'), 4.00 (apparent q, 1, H-4'), 4.16 (apparent t, 1, J$_{3',4'}$=3.9 Hz, H-3'), 4.50 (apparent t, 1, J$_{2',3'}$=5.0 Hz, H-2'), 5.09 (br s, 1, 5'-OH), 5.33 (br s, 1, 3'-OH), 5.60 (br s, 1, 2'-OH), 5.71 (s, 2, OCH$_2$Ar), 5.93 (apparent d, 1, H-1'), 8.15 (m, 2, Ar-H-3,6), 8.27 (apparent d, 1, Ar-H-5), 8.84 (s, 1, H-8), 8.91 (s, 1, H-2), 9.84, 10.48 (2 br s, 2, H-N⊕CH$_2$). $^{13}$C NMR (Me$_2$SO-d$_6$) δ 60.94 (C-5'), 70.04 (C-3'), 74.58 (C-2'), 76.36 (C-OCH$_2$Ar), 85.99 (C-4'), 87.81 (C-1'), 119.77 (C-5), 123.08, 123.14, 123.21 (2 C-CF$_3$, Ar-C-3), 128.04, 129.71, 130.03, 132.35 (Ar-C-2,4,5,6), 135.91 (Ar-C-1), 142.86 (C-8), 144.53 (C-2), 145.31 (C-4), 148.53 (C-6).

EXAMPLE 19

1-(2-Chlorobenzyloxy)adenosine, perchloric acid salt (2o) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 260 nm (12,690) at pH 1; 259 (12,550) at pH 7; 258 (12,510) at pH 13; MS (FAB) m/e 408 (M+1); IR 1689, 1509, 1220, 1100 (broad), 931, 860, 774, 769, 645, 640, 623 cm$^{-1}$; $^1$H NMR (Me$_2$SO-d$_6$)δ 3.58, 3.68 (2 m, 2, J$_{4',5'a}$=3.9 Hz, J$_{4',5'b}$=3.9 Hz, J$_{5'a,5'b}$=12.0 Hz, CH$_2$-5'), 3.99 (apparent q, 1, H-4'), 4.16 (apparent t, 1, J$_{3',4'}$=4.0 Hz, H-3'), 4.49 (apparent t, 1, J$_{2',3'}$=4.6 Hz, H-2'), 5.09 (br s, 1, 5'-OH), 5.31 (br s, 1, 3'-OH), 5.54 (s, 2, OCH$_2$Ar), 5.60 (br s, 1, 2'-OH), 5.93 (d, 1, J$_{1',2'}$=5.3 Hz, H-1'), 7.42-7.78 (m, 4, H-Ar), 8.70 (s, 1, H-2), 8.83 (s, 1, H-8), 9.82, 10.48 (2 br s; 2, H-N⊕H$_2$). $^{13}$C NMR (Me$_2$SO-d$_6$) δ 60.82 (C-5'), 69.91 (C-3'), 73.45 (C-2'), 78.14 (C-OCH$_2$Ar), 85.84 (C-4'), 87.71 (C-1'), 119.44 (C-5), 127.42, 129.50, 131.70 (Ar-C-3,4,5), 129.99 (Ar-C-2), 132.94 (Ar-C-6), 134.02 (Ar-C-1), 142.84 (C-8), 144.33 (C-2), 145.19 (C-4), 148.39 (C-6).

EXAMPLE 20

1-(3-Chlorobenzyloxy)adenosine, perchloric acid salt (2p) was prepared using the procedure set forth in Example 4. The amount of reactant used and the melting point and elemental analysis data are set forth in Table 2. UV, IR, $^1$H NMR. $^{13}$C NMR and mass spectrometer data are set forth herein.

UV $\lambda_{max}$ 259 nm (12,910) at ph 1; 259 (12,560) at pH 7; 258 (12,560) at pH 13; MS (FAB) m/e 408 (M+1); IR 1694, 1620, 1575, 1510, 1430, 1415, 1380, 1220, 1075 (broad), 885, 785, 685, 622 cm$^{-1}$; $^1$H NMR (Me$_2$SO-d$_6$)δ3.59, 3.69 (2 m, 2, J$_{4',5'a}$=3.9 Hz, J$_{4',5'b}$=4.0 Hz, J$_{5'a,5'b}$=12.0 Hz, CH$_2$-5'), 4.00 (apparent q, 1, H-4'), 4.17 (apparent t, 1, J$_{3+,4'}$=3.9 Hz, H-3'), 4.50 (apparent t, 1, J$_{2',3'}$=4.7 Hz, H-2'), 5.09 (br s, 1, 5'-OH), 5.33 (br s, 1, 3'-OH), 5.40 (s, 2, OCH$_2$Ar), 5.60 (br s, 1, 2'-OH), 5.96 (d, 1, J$_{1',2'}$=5.4 Hz, H-1'), 7.48-7.88 (m, 4, H-Ar), 8.82 (s, 1, H-8), 9.10 (s, 1, H-2), 9.78, 10.44 (2 br s, 1, H-N⊕H$_2$). $^{13}$C NMR (Me$_2$SO-d$_6$) δ 60.85 (C-5'), 69.95 (C-3'), 74.46 (C-2'), 80.63 (C-OCH$_2$Ar), 85.87 (C-4'), 87.78 (C-1'), 119.34 (C-5), 129.23, 129.54, 130.41 (Ar-C-2,4,6), 130.24 (Ar-C-5), 133.00 (Ar-C-3), 134.32 (Ar-C-1), 142.84 (C-8), 144.82 (C-2,), 145.20 (C-4), 148.26 (C-6).

EXAMPLE 21

1-(2-Nitrobenzyloxy)adenosine, perchloric acid salt (2q) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

US $\lambda_{max}$ 259 nm (18,170) at pH 1; 259 (18,090) at pH 7; 257 (16,890) at pH 13; MS (FAB) m/e 419 (M+1); IR 1685, 1538, 1530, 1510, 1347, 1105 (broad), 624 cm$^{-1}$; $^1$H NMR (Me$_2$SO-d$_6$) δ 3.59, 3.68 (2 m, 2, $J_{4',5'a}$=3.7 Hz $J_{4',5'b}$=4.0 Hz, $H_{5'a,5'b}$=12.1 Hz, CH$_2$-5'), 4.00 (apparent q, 1, H-4'), 4.16 (apparent t, 1, $J_{3',4'}$=3.9 Hz, H-3'), 4.49 (apparent t, 1, $J_{2',3'}$=4.9 Hz, H-2'), 5.08 (br s, 1, 5'-OH), 5.32 (br s, 1, 3'-OH), 5.60 (br s, 1, 2'-OH), 5.76 (s,2, OCH$_2$Ar), 5.95 (d, 1, $J_{1',2'}$=5.35 Hz, H-1'), 7.75 (m, 1, Ar-H-4), 7.90 (m, 1, Ar-H-5), 7.99 (apparent d, 1, Ar-H-3), 8.22 (apparent d, 1, Ar-H-6), 8.83 (s, 1, H-8), 8.94 (s, 1, H-2), 9.80, 10.46 (br s, 2, H-N⊕H$_2$). $^{13}$C NMR (Me$_2$SO-d$_6$) δ 60.83 (C-5'), 69.92 (C-3'), 74.46 (C-2'), 77.01 (C-OCH$_2$Ar), 85.84 (C-4'), 87.77 (C-1'), 119.54 (C-5), 124.81 (Ar-C-3), 128.32 (Ar-C-1), 130.29 (Ar-C-4), 131.11 (Ar-C-5), 134.03 (Ar-C-6), 142.79 (C-8), 144.45 (C-2), 145.21 (C-4), 147.54 (Ar-C-2), 148.36 (C-6).

EXAMPLE 22

1-(3-Nitrobenzyloxy)adenosine, perchloric acid salt (2r) was prepared using the procedure set forth in Example 4. The amount of reactant used and the melting point and elemental analysis data are set forth in Table 2. UV, IR, $^1$H NMR. $^{13}$C NMR and mass spectrometer data are set forth herein.

UV $\lambda_{max}$ 259 nm (19,400) at pH 1; 259 (19,100) at pH 7; 258 (17,560) at pH 13; MS (FAB) m/e 419 (M+1); IR 1691, 1620, 1533, 1511, 1352, 1225, 1090 (broad), 740, 622 cm$^{-1}$; $^1$H NMR (Me$_2$SO-d$_6$) δ 3.60, 3.71 (2 m, 2, $J_{4',5'a}$=$J_{4',5'b}$=3.9 Hz, $J_{5'a,5'b}$=12.0 Hz, CH$_2$-5'), 4.01 (apparent q, 1, H-4'), 4.18 (apparent t, 1, $J_{3',4'}$=3.7 Hz, H-3'), 4.51 (apparent t, 1, $J_{2',3'}$=4.8 Hz, H-2'), 5.10 (br s, 1, 5'-OH), 5.34 (br s, 1, 3'-OH), 5.55 (s, 2, OCH$_2$Ar), 5.60 (br s, 1, 2'-OH), 5.97 (d, 1, $J_{1',2'}$=5.4 Hz, H-1'), 7.80 (t, 1, H-Ar5), 8.17 (d, 1, H-Ar6), 8.35 (m, 1, H-Ar4), 8.67 (s, 1, H-Ar2), 8.83 (s, 1, H-8), 9.17 (s, 1, H-2), 10.15 (br s, 2, H-N⊕H$_2$). $^{13}$C NMR (Me$_2$SO-d$_6$) δ 60.88 (C-5') 69.99 (C-3'), 74.49 (C-2'), 80.11 (C-OCH$_2$Ar), 85.92 (C-4'), 87.79 (C-1'), 119.42 (C-5), 124.40 (Ar-C5), 125.45 (Ar-C4), 129.95 (Ar-C2), 134.13 (Ar-C6), 137.25 (Ar-C1), 142.87 (C-8), 144.95 (C-2), 145.24 (C-4), 147.64 (Ar-C3), 148.31 (C-6).

EXAMPLE 23

1-(4-Nitrobenzyloxy)adenosine, perchloric acid salt (2s) was prepared using the procedure set forth in Example 4. The amount of reactant used and the melting point and elemental analysis data are set forth in Table 2. UV, IR, $^1$H NMR. $^{13}$C NMR and mass spectrometer data are set forth herein.

UV $\lambda_{max}$ 260 nm (22,270) at pH 1; 260 (21,970) at pH 7; 265 (18,550) at pH 13 (slowly decreased); MS (FAB) m/e 419 (M+1); IR 1686, 1524, 1348, 1220, 1090 (broad), 854, 750, 622 cm$^{-1}$; $^1$H NMR (Me$_2$SO-d$_6$) δ 3.57, 3.70 (2 m, 2, $J_{4',5'a}$=4.0 Hz, $J_{4',5'b}$=3.9 Hz, $J_{5'a,5'b}$=12.0 Hz, CH$_2$-5'), 4.00 (apparent q, 1, H-4'), 4.16 (apparent q, 1, $J_{3',4'}$=3.7 Hz, H-3'), 4.50 (apparent q, 1, $J_{2',3'}$=4.9 Hz, H-2'), 5.09 (t, 1, $J_{5',5'-OH}$=5.3 Hz, 5'-OH), 5.34 (d, 1, $J_{3',3'-OH}$=5.2 Hz, 3'-OH), 5.55 (s, 2, OCH$_2$Ar), 5.60 (d, 1, $J_{2',2'-OH}$=6.1 Hz, 2'-OH), 5.95 (d, 1, $J_{1',2'}$=5.4 Hz, H-1'), 7.97 (d, 2, Ar-H-2,6), 8.34 (d, 2, Ar-H-3,5), 8.83 (s, 1, H-8), 9.11 (s, 1, H-2), 10.15 (broad 2, H-N⊕H$_2$). $^{13}$C NMR (Me$_2$SO-d$_6$) δ60.87 (C-5'), 69.97 (C-3'), 74.53 (C-2'), 80.03 (C-OCH$_2$Ar), 85.89 (C-4'), 87.84 (C-1'), 119.43 (C-5), 123.38 (Ar-C-3,5), 131.38 (Ar-C-2,6), 139.45 (Ar-C1), 142.88 (C-8), 144.76 (C-2), 145.24 (C-4), 148.01 (Ar-C4), 148.33 (C-6).

EXAMPLE 24

1-(2-Methoxy-5-nitrobenzyloxy)adenosine, perchloric acid salt (2t) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 259 nm (14,550) and 310 (10,620) at pH 1; 259 (14,510) and 310 (10,870) at pH 7; 311 (11,800) at pH 13; MS (FAB) m/e 449 (M+1); IR 1681, 1595, 1510, 1500, 1490, 1332, 1261, 1212, 1127, 1090 (broad), 1036, 900, 640, and 620 cm$^{-1}$; $^1$H NMR (Me$_2$SO-d$_6$) δ 3.59, 3.68 (2 m, 2, $J_{4',5'a}$=3.5 Hz, $J_{4',5'b}$=3.5 Hz, $J_{5'a,5'b}$=12.0 Hz, CH$_2$-5'), 3.86 (s, 3, CH$_3$OAr), 4.00 (apparent q, 1, H-4'), 4.16 (apparent t, 1, $J_{3',4'}$=4.0 Hz, H-3'), 4.49 (apparent t, 1, $J_{2',3'}$=4.1 Hz, H-2'), 5.09 (apparent t, 1, $J_{5',5'-OH}$=4.9 Hz, 5'-OH), 5.33 (apparent d, 1, $J_{3',3'-OH}$=5.0 Hz, 3'-OH), 5.50 (s, 2, OCH$_2$Ar), 5.59 (apparent d, 1, $J_{2',2'-OH}$=6.0 Hz, 2'-OH, 5.95 (d, 1, $J_{1',2'}$=5.34 Hz, H-1'), 7.31 (d, 1, Ar-H-3), 8.40 (apparent q, 1, Ar-H-4), 8.56 (d, 1, Ar-H-6), 8.84 (s, 2, H-2,8), 9.74, 10.35 (2 br s, 2, H-NH$_2$). $^{13}$C NMR (Me$_2$SO-d$_6$) δ 56.78 (C-ArOCH$_3$), 60.86 (C-5'), 69.96 (C-3'), 74.59 (C-2'), 75.61 (C-OCH$_2$Ar), 85.89 (C-4'), 87.89 (C-1'), 111.80 (Ar-C-3), 119.35 (C-5), 121.12, (Ar-C-1), 127.77, 128.24 (Ar-C-6,4), 140.31 (Ar-C-5), 142.93 (C-8), 144.52 (C-2), 145.25 (C-4), 148.39 (C-6), 163.21 (Ar-C-2).

EXAMPLE 25

1-(3-Methoxycarbonylbenzyloxy)adenosine, perchloric acid salt (2u) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 259 nm (12,670) at pH 1; 259 (12,670) at pH 7; 257 (13,410) at pH 13; MS (FAB) m/e 432 (M+1); IR 1710, 1684, 1435, 1315, 1294, 1214, 1100 (broad), 895, 765, and 624 cm$^{-1}$; $^1$H NMR (Me$_2$SO-d$_6$) δ 3.59, 3.69 (2 m, 2, $J_{4',5'a}$=3.7 Hz, $J_{4',5'b}$=3.9 Hz, $J_{5'a,5'b}$=12.1 Hz, CH$_2$-5'), 3.89 (s, 3, ArCO$_2$CH$_3$), 4.00 (apparent q, 1, H-4'), 4.16 (apparent t, 1, $J_{3',4'}$=3.7 Hz, H-3'), 4.50 (apparent t, 1, $J_{2',3'}$=4.8 Hz, H-2'), 5.10, 5.34, 5.61 (3 br s, 3, 5',3',2'-OH), 5.49 (s, 2, OCH$_2$Ar), 5.96 (d, 1, $J_{1',2'}$=5.4 Hz, H-1'), 7.64 (t, 1, Ar-H-5), 7.99, 8.06 (d, 2, Ar-H-6,4), 8.33 (s, 1, Ar-H-2), 8.83 (s, 1, H-8), 9.03 (s, 1, H-2), 9.82, 10.44 (2 br s, 2, H-N$^-$H$_2$). $^{13}$C NMR (Me$_2$SO-d$_6$) δ 52.21 (C-ArCO$_2$CH$_3$), 60.88 (C-5'), 69.99 (C-3'), 74.56 (C-2'), 81.02 (C-OCH$_2$Ar), 85.90 (C-4'), 87.87 (C-1'), 119.38 (C-5), 128.94 (Ar-C-5), 129.81 (Ar-C-3), 130.32, 131.40, 135.49 (Ar-C-6,4,2), 132.78 (Ar-C-1), 142.87 (C-8), 144.88 (C-2), 145.23 (C-4), 148.33 (C-6), 165.80 (C-ArCO$_2$CH$_3$).

EXAMPLE 26

1-(4-Cyanobenzyloxy)adenosine, perchloric acid salt (2v) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 259 nm (13,800) at pH 1; 259 (13,620) at pH 7; 258 (sh) at pH 13; MS (FAB) m/e 399 (M+1); IR 2240, 1687, 1510, 1420, 1385, 1225, 1215, 1075 (broad), 825, 621 cm$^{-1}$; $^1$H NMR (Me$_2$SO-d$_6$) δ 3.61, 3.73 (2 m, 2, $J_{4',5'a}$=3.9 Hz, $J_{4',5'b}$=5.6 Hz, $J_{5'a,5'b}$=12.0 Hz, CH$_2$-5'), 4.02 (apparent q, 1, H-4'), 4.19 (apparent q, 1, $J_{3',4'}$=3.7 Hz, H-3'), 4.51 (apparent q, 1, $J_{2',3'}$=4.8 Hz, H-2'), 5.11 (t, 1, $J_{5',5'-OH}$=5.3 Hz, 5'-OH), 5.35 (apparent d, 1, $J_{3',3'-OH}$=5.2 Hz, 3'-OH), 5.51 (s, 2, OCH$_2$Ar), 5.62 (apparent d, 1, $J_{2',2'-OH}$=6.1 Hz, 2'-OH), 5.97 (apparent d, 1, $J_{1',2'}$=5.4 Hz, H-1'), 7.90 (d, 2, Ar-H-3,5), 7.99 (d, 2, Ar-H-2,6), 8.83 (s, 1, H-8), 9.10 (s, 1, H-2), 10.15 (broad, 2,-H-N$^{61}$H$_2$). $^{13}$C NMR (Me$_2$SO-d$_6$) δ 60.84 (C-5'), 69.94 (C-3'), 74.51 (C-2'), 80.44 (C-OCH$_2$Ar), 85.85 (C-4'), 87.83 (C-1'), 112.16 (Ar-C4), 118.38 (C-C≡N), 119.39 (C-5), 131.03 (Ar-C-2,6), 132.26 (Ar-C-3,5), 137.43 (Ar-C1), 142.85 (C-8), 144.71 (C-2), 145.21 (C-4), 148.29 (C-6).

EXAMPLE 27

1-(2-Cyanobenzyloxy)adenosine, perchloric acid salt (2w) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 260 nm (12,700) at pH 1; 259 (12,560) at pH 7; 257 (12,160) at pH 13; MS (FAB) m/e 399 (M+1); IR 2250, 1684, 1505, 1222, 1100 (broad), 772, and 623 cm$^{-1}$; $^1$H NMR (Me$_2$SO-d$_6$) δ 3.59, 3.68 (2 m, 2, $J_{4',5'a}$=3.8 Hz, $J_{4',5'b}$=3.9 Hz, $J_{5'a,5'b}$=12.0 Hz, CH$_2$-5'), 3.99 (apparent q, 1, H-4'), 4.16 (apparent t, 1, $J_{3',4'}$=3.5 Hz, H-3'), 4.49 (apparent t, 1, $J_{2',3'}$=4.8 Hz, H-2'), 5.09 (br s, 1, 5'-OH), 5.33 (br s, 1, 3'-OH), 5.60 (br, 1, 2'-OH), 5.60 (s, 2, OCH$_2$Ar), 5.94 (apparent d, 1, $J_{1',2'}$=5.3 Hz, H-1'), 7.70 (t, 1, Ar-H, 4), 7.87, 7.90 (2 m, 2, Ar-H, 3,5), 7.99 (d, 1, Ar-H, 6), 8.81 (s, 1, H-2), 8.83 (s, 1, H-8), 9,92, 10.48 (2 br s, 2, H-N⊕H$_2$). $^{13}$C NMR (Me$_2$SO-d$_6$) δ 60.81 (C-5'), 69.89 (C-3'), 74.44 (C-2'), 78.56 (C-OCH$_2$-Ar), 85.83 (C-4'), 87.74 (C-1'), 112.53 (Ar-C-2), 117.12 (C-C≡N), 119.58 (C-5), 130.50, 131.71, 133.20, 133.38 (Ar-C-3,4,5,6), 135.16 (Ar-C-1), 142.81 (C-8), 144.23 (C-2), 145.16 (C-4), 148.38 (C-6).

EXAMPLE 28

1-(3-Cyanobenzyloxy)adenosine, perchloric acid salt (2x) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 259 nm (13,500) at pH 1; 259 (12,900) at pH 7; 57 (12,980) at pH 13; MS (FAB) m/e 399 (M+1); IR 2230, 1694, 1510, 1235, 1215, 1090 (broad), 892, 690, 655, 640 and 623 cm$^{-1}$; $^1$H NMR (Me$_2$SO-d$_6$) δ 3.59, 3.69 (2 m, 2, $J_{4',5'a}$=3.8 Hz, $J_{4',5'b}$=3.8 Hz, $J_{5'a,5'b}$=12.0 Hz, CH$_2$-5'), 4.00 (apparent q, 1, H-4'), 4.16 (apparent t, 1, $J_{3',4'}$=3.7 Hz, H-3'), 4.50 (apparent t, 1, $J_{2',3'}$=4.7 Hz, H-2'), 5.12 (br s, 1, 5'-OH), 5.34 (br s, 1, 3'-OH), 5.45 (s, 2, OCH$_2$Ar), 5.60 (br s, 1, 2'-OH), 5.96 (apparent d, 1, $J_{1',2'}$=5.4 Hz, H-1'), 7.69 (t, 1, Ar-H-5), 7.96, 8.02 (2 m, 2, Ar-H-4,6), 8.25 (s, 1, Ar-H-2), 8.83 (s, 1, H-8), 9.13 (s, 1, H-2), 9.78, 10.45 (2 br s, 2, H-N⊕H$_2$). $^{13}$C NMR (Me$_2$SO-d$_6$) δ 60.87 (C-5'), 69.97 (C-3'), 74.50 (C-2') 80.26 (C-OCH$_2$Ar), 85.90 (C-4'), 87.82 (C-1'), 111.44 (Ar-C-3), 118.31 (C-C≡N), 19.41 (C-5), 129.64 (Ar-C-5), 133.18 (Ar-C-4), 133.60 (Ar-C-1), 134.32 (Ar-C-2), 135.33 (Ar-C-6), 142.87 (C-8), 44.84 (C-2), 145.25 (C-4), 148.28 (C-6).

EXAMPLE 29

1-(2-methoxybenzyloxy)adenosine, perchloric acid salt (2y) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

The crude product (4.2 g) was dissolved in about 350 mL hot EtOH, treated with silica gel and filtered through a layer of silica gel. The clear solution was slowly diluted with OH until cloudy, chilled overnight, and the precipitate was collected. This product still contained NH$_4$+ according to the $^1$H NMR spectrum. However, a second crop obtained from the filtrate which was washed with ether and dried at 56° C. over phosphorus pentoxide overnight was found to be free of NH$_4$+. UV $\lambda_{max}$ 259 nm (12,800) at pH 1; 259 (12,600) at pH 7; 259 (13,000) at pH 13; MS (FAB) m/e 404 (M+1); IR 1684, 1605, 1505, 1500, 1250, 1225, 1100 (broad), 1025, 1015, 860, 624 cm$^{-1}$; $^1$H NMR (Me$_2$SO-d$_6$) δ 3.65 (s, 3, OCH$_3$), 3.57, 3.68 (2 m, 2, CH$_2$-5'), 3.99 (apparent q, 1, H-4'), 4.15 (apparent q, 1, H-3'), 4.47 (apparent q, 1, H-2'), 5.18 (apparent t, 1, OH-5'), 5.31 (apparent d, 1, OH-3'), 5.42 (s, 2, OCH$_2$Ar), 5.59 (apparent d, 1, OH-2'), 5.93 (d, 1, H-1'), 7.02 (m, 1, Ar-H-4,5), 7.48 (m, 2, Ar-H-3,6), 8.65 (s, 1, H-2), 8.80 (s, 1, H-8), 9.54, 10.44 (2 br s, 2, H-N⊕H$_2$).

EXAMPLE 30

1-(3,4-Dimethylbenzyloxy)adenosine, perchloric acid salt (2z) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 259 nm (13,300) at pH 1; 259 (13,300) at pH 7; 258 (13,600) at pH 13; MS (FAB) m/e 402 (M+1); IR 1691, 1510, 1100 (broad), 624 cm$^{-1}$; $^1$H NMR (Me$_2$SO-d$_6$) δ 2.25 (s, 6, Ar-CH$_3$), 3.58, 3.69 (2 m, 2, $J_{4',5'a}$=$J_{4',5'b}$=3.87 Hz, $J_{5'a,5'b}$=12.1 Hz, CH$_2$-5'), 4.00 (apparent q, 1, H-4'), 4.16 (apparent t, 1, $J_{3',4'}$=3.85 Hz, H-3'), 4.49 (apparent q, 1, $J_{2',3'}$=4.88 Hz, H-2'), 5.09 (br s, 1, OH-5'), 5.33 (s, 2, OCH$_2$Ar), 5.60 (br d, 1, $J_{2',2'-OH}$=4.57 Hz, OH-2'), 5.94 (d, 1, $J_{1',2'}$=5.4 Hz, H-1'), 8.81 (s, 1, H-8), 8.91 (s, 1, H-2), 9.72, 10.41 (2 br s, 2, H-N⊕H$_2$).

EXAMPLE 31

1-(3,5-Dimethylbenzyloxy)adenosine, perchloric acid salt (2aa) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 259 nm (12,900) at pH 1; 259 (13,100) at pH 7; 258 (13,000) at pH 13; MS (FAB) m/e 402 (M+1); IR 1693, 1510, 1225, 1100 (broad), 890, 853, 638, 623 cm$^{-1}$; $^1$H NMR (Me$_2$SO-d$_6$) δ 2.30 (s, 6, Ar-CH$_3$), 3.59, 3.69 (2 m, 2, $J_{4',5'a}$=3.8 Hz, $J_{4',5'b}$=3.9 Hz, $J_{5'a,5'b}$=12.0 Hz, CH$_2$-5'), 4.00 (apparent q, 1, H-4'), 4.16 (apparent t, 1, $J_{3',4'}$=3.8 Hz, H-3'), 4.49 (br s, 1, $J_{2',3'}$=4.9 Hz, H-2'), 5.09 (br s, 1, OH-5'), 5.32 (s, 2, OCH$_2$Ar), 5.60 (br d, 1, OH-2'), 5.95 (d, 1, $J_{1',2'}$=5.38 Hz, H-1'), 7.11, 7.28 (2 s, 3, Ar-H), 8.82 (s, 1, H-8), 8.96 (s, 1, H-2), 9.72, 10.42 (2 br s, 2, H-N⊕H$_2$).

EXAMPLE 32

1-(2,5-Dimethylbenzyloxy)adenosine, perchloric acid salt (2bb) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 259 nm (13,100) at pH 1; 259 (13,200) at pH 7; 258 (13,200) at pH 13; MS (FAB) m/e 402 (M+1); IR 1688, 1508, 1415, 1225, 1100 (broad), 915, 900, 880, 875, 825, 685, 655, 622 cm$^{-1}$; $^1$H NMR (Me$_2$SO-d$_6$) δ 2.26, 2.39 (2 s, 6, Ar-CH$_3$), 3.58, 3.68 (2 m, 2, J$_{4,5'a}$=J$_{4',5'b}$=3.8 Hz, J$_{5'a,5'b}$=12.1 Hz, CH$_2$-5'), 3.99 (apparent q, 1, H-4'), 4.15 (apparent t, 1, J$_{3',4'}$=3.9 Hz, H-3'), 4.48 (apparent q, 1, J$_{2',3'}$=4.9 Hz, H-2'), 5.09 (br s, 1, OH-5'), 5.32 (br s, 1, OH-3'), 5.41 (s, 2, OCH$_2$Ar), 5.59 (apparent d, 1, OH-2'), 5.93 (d, 1, J$_{1',2'}$=5.37 Hz, H-1'), 7.18, 7.20, 7.30 (m, 3, H-Ar), 8.65 (s, 1, H-2), 8.82 (s, 1, H-8), 9.75 10.45 (2 br s, 2, H-N⊕H$_2$).

EXAMPLE 33

1-(2,4-Dimethylbenzyloxy)adenosine, perchloric acid salt (2cc) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 259 nm (13,300) at pH 1; 259 (13,400) at pH 7; 258 (13,200) at pH 13; MS (FAB) m/e 402 (M+1); IR 1689, 1615, 1510, 1430, 1220, 1100 (broad), 895, 645, 623 cm$^{-1}$; $^1$H NMR (Me$_2$SO-d$_6$) δ 2.31, 2.42 (2 s, 6, Ar-CH$_3$), 3.57, 3.67 (2 m, 2, CH$_2$-5'), 3.98 (apparent q, 1, H-4'), 4.15 (apparent t, 1, H-3'), 4.48 (apparent t, 1, H-2'), 5.09 (br s, 1, OH-5'), 5.33 (br s, 1, OH-3'), 5.40 (s, 2, OCH$_2$Ar), 5.60 (br s, 1, OH-2'), 5.91 (d, 1, J$_{1',2'}$=5.35 Hz, H-1'), 7.03, 7.15, 7.31 (m, 3, H-Ar), 8.52 (s, 1, H-2), 8.82 (s, 1, H-8), 9.76 10.45 (2 br s, 2, H-N⊕H$_2$).

EXAMPLE 34

1-Benzyloxyadenosine, perchloric acid salt (2dd) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 259 nm (13,100) at pH 1; 259 (13,200) at pH 7; 257 (13,100) at pH 13; MS (FAB) m/e 374 (M+1); IR 1686, 1515, 1415, 1230, 1100 (broad), 755, 622 cm$^{-1}$; $^1$H NMR (Me$_2$SO-d$_6$) δ 3.58, 3.68 (2 m, 2, J$_{4',5'a}$=3.9 Hz, J$_{4',5'b}$=3.9 Hz, J$_{5'a,5'b}$=12.1 Hz, CH$_2$-5'), 3.99 (apparent q, 1, H-4'), 4.15 (apparent q, 1, J$_{3',4'}$=3.9 Hz, H-3'), 4.49 (apparent q, 1, J$_{2',3'}$=4.9 Hz, H-4'), 5.18 (apparent t, 1, J$_{5',5'-OH}$=5.1 Hz, OH-5'), 5.33 (d, 1, J$_{3',3'-OH}$=5.1 Hz, OH-3'), 5.42 (s, 2, OCH$_2$Ar), 5.60 (d, 1, J$_{2',2'-OH}$=6.1 Hz, OH-2'), 5.94 (d, 1, J$_{1',2'}$=5.4 Hz, H-1'), 7.48, 7.66 (2 m, 5, H-Ar), 8.82 (s, 1, H-8), 8.97 (s, 1, H-2).

EXAMPLE 35

1-(2,6-Difluorobenzyloxy)adenosine, perchloric acid salt (2ee) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 259 nm (14,000) at pH 1; 259 (13,900) at pH 7; 257 (13,400) at pH 13; MS (FAB) m/e 410 (M+1); IR 1685, 1629, 1515, 1476, 1415, 1405, 1245, 1230, 1100 (broad), 920, 910, 800, 675, 622 cm$^{-1}$; $^1$H NMR (Me$_2$SO-d$_6$) δ 3.58, 3.68 (2 m, 2, J$_{4',5'a}$=3.9 Hz, J$_{4',5'b}$=4.0 Hz, J$_{5'a,5'b}$=12.1 Hz, CH$_2$-5'), 3.99 (apparent q, 1, H-4'), 4.16 (apparent t, 1, J$_{3',4'}$=3.9 Hz, H-3'), 4.49 (apparent q, 1, J$_{2',3'}$=4.9 Hz, H-2'), 5.10 (br s, 1, OH-5'), 5.33 (br s, 1, OH-3'), 5.57 (s, 2, OCH$_2$Ar), 5.62 (apparent d, 1, OH-2'), 5.94 (d, 1, H-1'), 7.23 (t, 2, H-Ar-3,5), 7.63 (m, 1, H-Ar-4), 8.83 (s, 1, H-8), 8.87 (s, 1, H-2), 9.83, 10.48 (2 br s, 2, H-N⊕H$_2$).

EXAMPLE 36

1-(3,5-Difluorobenzyloxy)adenosine, perchloric acid salt (2ff) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 259 nm (13,600) at pH 1; 259 (13,500) at pH 7; 257 (12,700) at pH 13; MS (FAB) m/e 410 (M+1); IR 1697, 686 (sh), 1630, 1605, 1455, 1380, 1330, 1230, 1100 (broad), 870, 860 (sh), 845, 665, 624 cm$^{-1}$; $^1$H NMR (Me$_2$SO-d$_6$) δ 3.59, 3.70 (2 m, 2, J$_{4',5'a}$=3.9 Hz, J$_{4',5'b}$=4.0 Hz, J$_{5'a,5'b}$=12.0 Hz, CH$_2$-5'), 4.01 (apparent q, 1, H-4'), 4.17 (apparent d, 1, J$_{3',4'}$=3.8 Hz, H-3'), 4.50 (apparent q, 1, J$_{2',3'}$=4.9 Hz, H-2'), 5.10 (br s, 1, OH-5'), 5.34 (apparent d, 1, H-3), 5.40 (s, 2, OCH$_2$Ar), 5.61 (apparent d, 1, J$_{2',2'-OH}$=6.1 Hz, OH-2'), 5.96 (d, 1, J$_{1',2'}$=5.4 Hz, H-1'), 7.39 (m, 1, H-Ar-4), 7.50 (m, 2, H-Ar-2,6), 8.83 (s, 1, H-8), 9.07 (s, 1, H-2), 9.78, 10.47 (2 br s, 2, H-N⊕H$_2$).

EXAMPLE 37

1-(2,5-Difluorobenzyloxy)adenosine, perchloric acid salt (2 gg) was prepared using the procedure set forth in Example 4. The amount of reactant used and the melting point and elemental analysis data are set forth in Table 2. UV, IR, $^1$H NMR, $^{13}$C NMR and mass spectrometer data are set forth herein.

UV $\lambda_{max}$ 260 nm (13,800) at pH 1; 260 (13,800) at pH 7; 258 (13,200) at pH 13; MS (FAB) m/e 410 (M+1); IR 1691, 1510, 1500, 1435, 1240, 1230, 1195, 1100 (broad), 975, 880, 735, 624 cm$^{-1}$; $^1$H NMR (Me$_2$SO-d$_6$) δ 3.59, 3.70 (2 m, 2, J$_{4',5'a}$=3.9 Hz, J$_{4',5'b}$=4.0 Hz, J$_{5'a,5'b}$=12.0 Hz, CH$_2$-5'), 4.01 (apparent q, 1, H-4'), 4.17 (apparent q, 1, J$_{3',4'}$=3.8 Hz, H-3'), 4.50 (apparent q, 1, J$_{2',3'}$=4.9 Hz, H-2'), 5.11 (t, 1, J$_{5',5'-OH}$=5.3 Hz, OH-5'), 5.35 (d, 1, J$_{3',3'-OH}$=5.2 Hz, OH-3'), 5.49 (s, 2, OCH$_2$Ar), 5.63 (d, 1, J$_{2',2'-OH}$=6.1 Hz, OH-2'), 5.96 (d, 1, J$_{1',2'}$=5.4 Hz, H-1'), 7.40, 7.64 (2 m, 3, H-Ar), 8.83 (s, 1, H-8), 8.89 (s, 1, H-2).

In Table 1, Ado is adenosine, dAdo is 2-deoxyadenosine, N$^6$-Me-Ado is 6-methylamino-9-β-D-ribofuranosylpurine, Ado-N$^1$-Ox is Adenosine-N$^1$-oxide, MeOh is methanol and MCPBA is m-chloroperoxybenzoic acid.

In Table 2, N'-Oxide is adenosine-N$^1$-oxide. BrCH$_2$R is the appropriate benzyl bromide for the product shown. DMAc is N,N-dimethyl acetamide.

TABLE 1

| Product | Nucleoside | MCPBA | MeOH | Yield | Mp cap. | MF C, H, N Theory | Found |
|---|---|---|---|---|---|---|---|
| Ado-$N^1$-Ox (1a) | Ado 5 g (18.7 mmol) | 5.4 g | 500 mL | 3.7 g (70%) | 222–225° C. | $C_{10}H_{13}N_5O_5$ C = 42.40, H = 4.63, N = 24.73 | C = 42.45 H = 4.64 N = 24.66 |
| dAdo-$N^1$-Ox (1b) | dAdo 1.0 g (3.72 mmol) | 1.2 g | 100 mL | 1.0 g (100%) | 219–221° C. dec. | $C_{10}H_{13}N_5O_4 \cdot 0.40H_2O$ C = 43.76, H = 5.07, N = 25.52 | C = 43.83 H = 5.06 N = 25.28 |
| $N^6$-Me-Ado-$N^1$-Ox (1c) | $N^6$-Me-Ado 2.0 g (7.12 mmol) | 3.5 g | 80 mL | 620 mg (30%) | 142–152° C. | $C_{11}H_{15}N_5O_5 \cdot 0.25CHCl_3 \cdot 0.30EtOH$ C = 42.03, H = 5.08, N = 20.68 | C = 42.12 H = 5.02 N = 20.74 |

TABLE 2

Substituted N'-Benzyloxyadenosines

| Product | | N'-Oxide | BrCH₂R | DMAc | NH₄ClO₄ | Yield (%) | M.P. Cap | M.F. C, H, N, Theory | Found |
|---|---|---|---|---|---|---|---|---|---|
| 2a | Ado—N¹OCH₂—C₆H₄—CH₃ (para) | 2.7 g (9.54 mmol) | 8.82 g (47.7 mmol) | 60 mL | 5.85 g 25 mL H₂O | 2.6 (56%) | 116–118° C. | C₁₈H₂₂ClN₅O₉·H₂O C = 42.74, H = 4.78, N = 13.85 | C = 42.70 H = 4.67 N = 13.70 |
| 2b | Ado—N¹OCH₂—C₆H₄—CH₃ | 2.5 g (8.83 mmol) | 4.9 g (26.5 mmol) | 50 mL | 5 g 25 mL H₂O | 1.9 (44%) | 117–122° C. dec. | C₁₈H₂₂ClN₅O₉·0.25H₂O C = 43.91, H = 4.61, N = 14.22 | C = 44.06 H = 4.66 N = 14.36 |
| 2c | Ado—N¹OCH₂—C₆H₄(H₃C) | 3.0 g (10.6 mmol) | 9.8 g (53 mmol) | 60 mL | 6.25 g 25 mL H₂O | 4.0 (77%) | 122–125° C. dec. | C₁₈H₂₂ClN₅O₉·0.75H₂O C = 43.12, H = 4.72, N = 13.97 | C = 43.18 H = 4.67 N = 14.18 |
| 2d | Ado—N¹OCH₂—C₆H₄—OCH₃ | 2.5 g (8.83 mmol) | 5 mL | 50 mL | 5 g 25 mL H₂O | 2.4 (55%) | 123–129° C. | C₁₈H₂₂ClN₅O₁₀·H₂O C = 41.43, H = 4.64, N = 13.42 | C = 41.33 H = 4.68 N = 13.32 |
| 2e | Ado—N¹OCH₂—C₆H₄(OCH₃) | 2.5 g (8.83 mmol) | 5.0 g | 50 mL | 5 g 25 mL H₂O | 2.3 (52%) | 109–119° C. | C₁₈H₂₂ClN₅O₁₀·1.25H₂O C = 41.07, H = 4.50, N = 13.31 | C = 40.86 H = 4.60 N = 13.32 |
| 2f | Ado—N¹OCH₂—CH(CH₃)—C₆H₅ | 2.5 g (8.83 mmol) | 5 mL | 50 mL | 5 g 25 mL H₂O | 1.7 (40%) | 128–133° C. | C₁₈H₂₂ClN₅O₉·H₂O C = 42.74, H = 4.78, N = 13.84 | C = 42.66 H = 4.71 N = 13.96 |
| 2g | Ado—N¹OCH₂—C₆H₄—F | 2.5 g (8.83 mmol) | 5.0 g | 50 mL | 5 g 25 mL H₂O | 3.3 (77%) | 110–116° C. | C₁₇H₁₉ClFN₅O₉·H₂O C = 40.05, H = 4.15, N = 13.74 | C = 40.16 H = 4.08 N = 13.79 |

TABLE 2-continued

Substituted N¹-Benzyloxyadenosines

| Product | | N¹-Oxide | BrCH₂R | DMAc | NH₄ClO₄ | Yield (%) | M.P. Cap | M.F. C, H, N, Theory | Found |
|---|---|---|---|---|---|---|---|---|---|
| 2h | Ado—N¹OCH₂—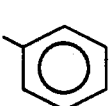 (3-F-C₆H₄) | 2.5 g 8.83 mmol | 5.0 g | 50 mL | 5 g 25 mL H₂O | 3.3 g (77%) | 106–114° C. | $C_{17}H_{19}ClFN_5O_9 \cdot H_2O$ C = 40.05, H = 4.15, N = 13.74 | C = 40.20 H = 4.03 N = 13.81 |
| 2i | Ado—N¹OCH₂—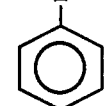 (4-F-C₆H₄) | 3.0 g (10.6 mmol) | 10 g (53.0 mmol) | 60 mL | 6.2 g 25 mL H₂O | 2.3 g (44%) | 143–146° C. | $C_{17}H_{19}ClFN_5O_9 \cdot 0.75H_2O$ C = 40.40, H = 4.09, N = 13.86 | C = 40.20 H = 4.13 N = 13.99 |
| 2j | Ado—N¹OCH₂—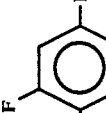 (2,4-F₂-C₆H₃) | 2.5 g (8.83 mmol) | 5.0 g (24.2 mmol) | 50 mL | 5 g 25 mL H₂O | 1.7 g (38%) | 116–120° C. | $C_{17}H_{18}ClF_2N_5O_9 \cdot H_2O$ C = 38.68, H = 3.82, N = 13.27 | C = 38.58 H = 3.66 N = 13.40 |
| 2k | Ado—N¹OCH₂—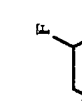 (3,4-F₂-C₆H₃) | 2.5 g (8.83 mmol) | 5.0 g (24.2 mmol) | 50 mL | 5 g 25 mL H₂O | 1.1 g (24%) | 116–122° C. | $C_{17}H_{18}ClF_2N_5O_9 \cdot 0.75H_2O$ C = 39.02, H = 3.76, N = 13.38 | C = 38.98 H = 3.60 N = 13.48 |
| 2l | Ado—N¹OCH₂—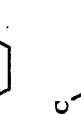 (2-CF₃-C₆H₄) | 3.0 g (10.6 mmol) | 10.5 g (43.9 mmol) | 85 mL | 6.2 g 25 mL H₂O | 3.0 g (53%)& | 108–111° C. | $C_{18}H_{19}ClF_3N_5O_9 \cdot 1.5H_2O$ C = 38.00, H = 3.90, N = 12.31 | C = 37.86 H = 3.87 N = 12.35 |
| 2m | Ado—N¹OCH₂—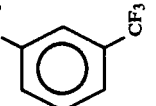 (3,5-(CF₃)₂-C₆H₃) | 2.5 g (8.83 mmol) | 5.0 g (16.3 mmol) | 50 mL | 5 g 25 mL H₂O | 3.3 g (61%) | 113–124° C. dec. | $C_{19}H_{18}ClF_6N_5O_9 \cdot 0.75H_2O$ C = 36.61, H = 3.15, N = 11.24 | C = 36.66 H = 3.09 N = 11.32 |

TABLE 2-continued

Substituted N'-Benzyloxyadenosines

| Product | | N'-Oxide | BrCH$_2$R | DMAc | NH$_4$ClO$_4$ | Yield (%) | M.P. Cap | M.F. C, H, N, Theory | Found |
|---|---|---|---|---|---|---|---|---|---|
| 2n | Ado—N$^1$OCH$_2$—⟨C$_6$H$_3$(CF$_3$)(CF$_3$)⟩ | 2.5 g (8.83 mmol) | 5.0 g (16.3 mmol) | 50 mL | 5 g 25 mL H$_2$O | 1.9 g (35%) | 114–119° C. dec. | C$_{19}$H$_{18}$ClF$_6$N$_5$O$_9$·0.25H$_2$O C = 37.15, H = 3.04, N = 11.40 | C = 37.02 H = 3.12 N = 11.38 |
| 2o | Ado—N$^1$OCH$_2$—⟨C$_6$H$_4$Cl (ortho)⟩ | 2.5 g (8.83 mmol) | 5.0 g (24.3 mmol) | 50 mL | 5 g 25 mL H$_2$O | 3.6 g (80%) | 126–130° C. dec. | C$_{17}$H$_{19}$Cl$_2$N$_5$O$_9$·0.25H$_2$O C = 39.82, H = 3.83, N = 13.66 | C = 39.86 H = 3.82 N = 13.79 |
| 2p | Ado—N$^1$OCH$_2$—⟨C$_6$H$_4$Cl (meta)⟩ | 2.5 g (8.83 mmol) | 5.0 g (24.3 mmol) | 50 mL | 5 g 25 mL H$_2$O | 3.5 g (78%) | 140–145° C. dec. | C$_{17}$H$_{19}$Cl$_2$N$_5$O$_9$·0.50H$_2$O C = 39.48, H = 3.90, N = 13.54 | C = 39.52 H = 3.80 N = 13.62 |
| 2q | Ado—N$^1$OCH$_2$—⟨C$_6$H$_4$NO$_2$ (ortho)⟩ | 2.5 g (8.83 mmol) | 5.7 g (26.5 mmol) | 50 mL | 5 g 25 mL H$_2$O | 2.19 g (47%) | 117–124° C. dec. | C$_{17}$H$_{19}$ClN$_6$O$_{11}$·H$_2$O C = 38.03, H = 3.92, N = 15.66 | C = 38.12 H = 3.78 N = 15.86 |
| 2r | Ado—N$^1$OCH$_2$—⟨C$_6$H$_4$NO$_2$ (meta)⟩ | 3.0 g (10.6 mmol) | 11.4 g (53 mmol) | 60 mL | 6.25 g 25 mL H$_2$O | 2.1 g (38%) | 128–132° C. dec. | C$_{17}$H$_{19}$ClN$_6$O$_{11}$·0.50H$_2$O C = 38.68, H = 3.76, N = 15.92 | C = 38.64 H = 3.84 N = 15.80 |
| 2s | Ado—N$^1$OCH$_2$—⟨C$_6$H$_4$NO$_2$ (para)⟩ | 2.5 g (8.83 mmol) | 9.5 g (44.2 mmol) | 50 mL | 5.2 g 20 mL H$_2$O | 3.2 g (70%) | 112–122° C. dec. | C$_{17}$H$_{19}$ClN$_6$O$_{11}$·0.50H$_2$O C = 38.68, H = 3.76, N = 15.92 | C = 38.72 H = 3.78 N = 15.88 |

TABLE 2-continued

Substituted N'-Benzyloxyadenosines

| Product | | N'-Oxide | BrCH₂R | DMAc | NH₄ClO₄ | Yield (%) | M.P. Cap | M.F. C, H, N, Theory | Found |
|---|---|---|---|---|---|---|---|---|---|
| 2t | Ado—N¹OCH₂— (phenyl with H₃CO and NO₂) | 2.5 g (8.83 mmol) | 5.0 g (20.3 mmol) | 50 mL | 5 g 25 mL H₂O | 4.0 g (83%) | 200–208° C. | C₁₈H₂₁ClN₆O₁₂ C = 39.39, H = 3.86, N = 15.31 | C = 39.43 H = 3.86 N = 15.30 |
| 2u | Ado—N¹OCH₂— (phenyl with COOCH₃) | 2.5 g (8.83 mmol) | 5.0 g (21.8 mmol) | 50 mL | 5 g 25 mL H₂O | 3.6 g (77%) | 176–181° C. dec. | C₁₉H₂₂ClN₅O₁₁·0.25H₂O C = 42.55, H = 4.23, N = 13.06 | C = 42.54 H = 4.18 N = 13.04 |
| 2v | Ado—N¹OCH₂— (phenyl with CN para) | 2.0 g (7.04 mmol) | 4.3 g (21.9 mmol) | 40 mL | 4.2 g 15 mL H₂O | 2.74 g (78%) | 112–118° C. dec. | C₁₈H₁₉ClN₆O₉·H₂O C = 41.83, H = 4.10, N = 16.26 | C = 41.60 H = 3.98 N = 16.20 |
| 2w | Ado—N¹OCH₂— (phenyl with CN) | 2.5 g (8.83 mmol) | 5.19 g (26.5 mmol) | 50 mL | 5 g 25 mL H₂O | 3.5 g (79%) | 117–124° C. | C₁₈H₁₉ClN₆O₉·0.25H₂O C = 42.95, H = 3.90, N = 16.70 | C = 42.84 H = 3.92 N = 16.63 |
| 2x | Ado—N¹OCH₂— (phenyl with CN) | 2.5 g (8.83 mmol) | 5.19 g (26.5 mmol) | 50 mL | 5 g 25 mL H₂O | 3.2 g (73%) | 130–135° C. | C₁₈H₁₉ClN₆O₉·0.50H₂O C = 42.52, H = 3.97, N = 16.55 | C = 42.42 H = 3.90 N = 16.48 |
| 2y | Ado—N¹OCH₂— (phenyl with OCH₃) | 2.5 g (8.83 mmol) | 5 g | 40 mL | 5 g 25 mL H₂O | 900 mg (20%) | 157–162° C. | C₁₈H₂₂ClN₅O₁₀·0.25Et₂O C = 43.68, H = 4.73, N = 13.41 | C = 43.72 H = 4.56 N = 13.34 |

TABLE 2-continued
Substituted N¹-Benzyloxyadenosines

| Product | | N¹-Oxide | BrCH₂R | DMAc | NH₄ClO₄ | Yield (%) | M.P. Cap | M.F. C, H, N, Theory | Found |
|---|---|---|---|---|---|---|---|---|---|
| 2z | Ado—N¹OCH₂—(3,4-diMe-phenyl)  | 1.5 g (5.32 mmol) | 3 mL | 30 mL | 3 g 15 mL H₂O | 2.25 g (84%) | 139-142° C. | C₁₉H₂₄ClN₅O₉·H₂O C = 43.89, H = 5.04, N = 13.47 | C = 44.00 H = 5.02 N = 13.38 |
| 2aa | Ado—N¹OCH₂—(3,5-diMe-phenyl) 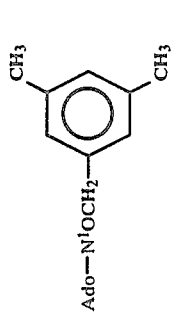 | 2.5 g (8.83 mmol) | 5 g | 50 mL | 5 g 25 mL H₂O | 3.5 g (80%) | 154-158° C. | C₁₉H₂₄ClN₅O₉·0.625H₂O C = 44.47, H = 4.96, N = 13.65 | C = 44.46 H = 5.11 N = 13.74 |
| 2bb | Ado—N¹OCH₂—(2,5-diMe-phenyl) 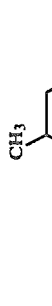 | 1.5 g (5.32 mmol) | 2 mL | 30 mL | 3 g 15 mL H₂O | 1.8 g (67%) | 117-123° C. | C₁₉H₂₄ClN₅O₉·H₂O C = 43.89, H = 5.04, N = 13.47 | C = 43.96 H = 5.12 N = 13.58 |
| 2cc | Ado—N¹OCH₂—(2,4-diMe-phenyl)  | 2.0 g (7.09 mmol) | 3 mL | 30 mL | 4 g 20 mL H₂O | 1.1 g (31%) | 120-130° C. | C₁₉H₂₄ClN₅O₉·0.75H₂O C = 44.28, H = 4.99, N = 13.59 | C = 44.38 H = 4.90 N = 13.65 |
| 2dd | Ado—N¹OCH₂—phenyl 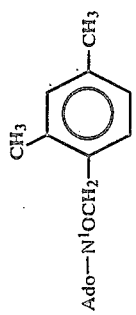 | 2.5 g (8.83 mmol) | 4.5 g | 50 mL | 5 g 25 mL H₂O | 3.1 g (74%) | 150-154° C. | C₁₇H₂₀ClN₅O₉·H₂O·0.10Et₂O C = 41.86, H = 4.64, N = 14.03 | C = 42.00 H = 4.50 N = 14.12 |
| 2ee | Ado—N¹OCH₂—(2,6-diF-phenyl) 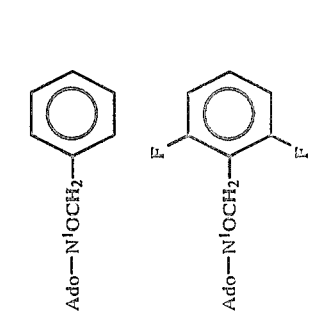 | 2.5 g (8.83 mmol) | 5 g | 50 mL | 5 g 25 mL H₂O | 1.75 g (39%) | 114-122° C. | C₁₇H₁₈ClF₂N₅O₉·H₂O C = 38.68, H = 3.82, N = 13.27 | C = 38.81 H = 3.81 N = 13.24 |

TABLE 2-continued
Substituted N¹-Benzyloxyadenosines
| Product | N'-Oxide | BrCH₂R | DMAc | NH₄ClO₄ | Yield (%) | M.P. Cap | M.F. C, H, N, Theory | Found |
|---|---|---|---|---|---|---|---|---|
| 2ff Ado—N¹OCH₂—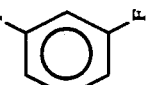 | 2.5 g (8.83 mmol) | 5 g | 50 mL | 5 g 25 mL H₂O | 2.0 g (44%) | 129–134° C. | C₁₇H₁₈ClF₂N₅O₉·0.625H₂O C = 39.18, H = 3.72, N = 13.44 | C = 39.22 H = 3.74 N = 13.36 |
| 2gg Ado—N¹OCH₂—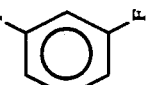 | 2.5 g (8.83 mmol) | 5 g | 50 mL | 5 g 25 mL H₂O | 3.4 g (76%) | 108–118° C. | C₁₇H₁₈ClF₂N₅O₉·0.75H₂O C = 39.02, H = 3.76, H = 13.38 | C = 39.00 H = 3.76 N = 13.30 |
Ado = adenosine.

EXAMPLE 29

Antiviral Activity of Adenosine-N'-Oxides and Substituted 1-(Benzyloxy)adenosines in Vero cells Adenosine-N'-oxides and substituted 1-(benzyloxy) adenosines were tested against vaccinia viruses that replicate in mammalian cells growing in cell culture. The results of these tests in Vero cells are summarized in Table 3. The Virus Rating (VR) is a standard weighted measurement of antiviral activity which takes into account the degree of inhibition of virus-induced cytopathogenic effects (CPE) and the degree of cytotoxicity produced by the test compound, determined by a modification of the method of R. W. Sidwell and N. J. Huffman, *Appl. Microbiol.*, 22, 797–801 (1971).

In tests carried out by this method, a greater value of VR indicates greater antiviral activity. A compound with a VR of 1.0 or greater is considered to have significant antiviral activity with a high degree of reproducibility in confirmatory in vitro tests. A compound with a VR of 0.5–0.9 is considered to have possible or marginal activity; a compound with a VR of less than 0.5 is considered to be inactive.

The $MIC_{50}$ (minimum inhibitory concentration, 50%) is the concentration of a test compound required for 50% inhibition of virus-induced cytopathogenic effect calculated by using a regression analysis program for semilog curve fitting. MTC (minimum toxic concentration) is the minimum drug concentration (μg/ml) causing any cytotoxicity. TI is the therapeutic index, calculated by dividing the minimum cytotoxic drug concentration (MTC) by the minimum inhibitory concentration, 50% ($MIC_{50}$). The results were compared with the commercial antiviral agent 9-β-D-arabinofuranosyladenine (Ara-A). The tests summarized in Table 3 show that definite antiviral activity against vaccinia virus is exhibited by the compounds tested.

TABLE 3

Activity vs Vaccinia Virus Substituted-Benzyloxy Derivatives (grouped by substituents)

| Compd. | Base | R | $V_r{}^a$ | $ID_{50}{}^b$ | $MTC^c$ | $TI^d$ |
|---|---|---|---|---|---|---|
| 1a | Ado—$N^1$—O | — | >2.4 | 0.32 | 100 | 312 |
| 1b | dAdo—$N^1$—O | — | >1.7 | 3.06 | >320 | 104 |
| 1c | $N^6$—MeAdo—$N^1$—O | — | >2.4 | 0.45 | 320 | 708 |
| 2a | Ado—$N^1$—O | 3-$CH_3$ | >2.4 | 0.41 | >320 | 781 |
|    |    |    |    | 0.66 |    | 487 |
| 2b | " | 4-$CH_3$ | 2.4 | 0.11 | 100 | 917 |
| 2c | " | 2-$CH_3$ | >2.4 | 0.32 | >320 | 1000 |
| 2d | " | 4-$OCH_3$ | 3.3 | 0.01 | 100 | 10000 |
|    |    |    | >3.0 |    | 10 | 1167 |
|    |    |    | 2.8 |    | 32 | 2805 |
| 2e | " | 3-$OCH_3$ | >2.8 | 0.20 | >320 | 1609 |
|    |    |    | >2.6 | 0.30 |    | 1075 |
| 2f | " |  | >2.7 | <0.32 | >320 | 1000 |
|    |    |    | >2.4 | 0.33 | >100 | 306 |
| 2g | " | 2-F | >1.7 | 4.97 | >320 | 64 |
|    |    |    | >1.5 | 9.48 |    | 34 |
| 2h | " | 3-F | >2.3 | 0.98 | >320 | 325 |
|    |    |    | >2.2 | 1.12 |    | 285 |
| 2i | " | 4-F | >2.1 | 2.41 | >320 | 133 |
|    |    |    | >2.0 | 2.00 |    | 160 |
| 2j | " | 2,4-F | >2.4 | 0.31 | >320 | 1029 |
| 2k | " | 3,4-F | >2.3 | 0.48 | >320 | 671 |
|    |    |    | >2.3 | 0.74 |    | 434 |
| 2l | " | 2-$CF_3$ | >2.2 | 0.82 | >320 | 391 |
| 2m | " | 3,5-$CF_3$ | >2.1 | 1.03 | >320 | 311 |
|    |    |    | >2.0 | 1.02 |    | 314 |
| 2n | " | 2,4-$CF_3$ | >2.0 | 1.45 | >320 | 221 |
|    |    |    | >1.9 | 1.77 |    | 181 |
| 2o | " | 2-Cl | >2.2 | 1.01 | >320 | 318 |
|    |    |    | >1.9 | 1.27 |    | 251 |
| 2p | " | 3-Cl | >2.0 | 1.08 | >320 | 295 |
|    |    |    | >1.9 | 1.66 |    | 193 |
| 2q | " | 2-$NO_2$ | >2.1 | 1.03 | >320 | 310 |
|    |    |    | >1.9 | 1.77 |    | 181 |
| 2r | " | 3-$NO_2$ | >1.2 | 10.0 | >320 | 32 |
|    |    |    | >1.1 | 10.7 |    | 30 |
| 2s | " | 4-$NO_2$ | >1.7 | 2.34 | >320 | 137 |
|    |    |    | >1.7 | 3.59 |    | 89 |
| 2t | " | 2-$OCH_3$ | >2.0 | 2.01 | >320 | 160 |
|    |    | 5-$NO_2$ | >1.6 | 3.68 |    | 87 |
| 2u | " | 3-$COOCH_3$ | >2.0 | 1.55 | >320 | 207 |
|    |    |    | >1.8 | 2.30 |    | 139 |
| 2v | " | 4-CN | >1.8 | 3.20 | >320 | 100 |
|    |    |    | >1.7 | 2.40 |    | 134 |
| 2w | " | 2-CN | >2.0 | 1.55 | >320 | 207 |
|    |    |    | >1.4 | 6.37 |    | 50 |
| 2x | " | 3-CN | >2.0 | 0.76 | >320 | 182 |
|    |    |    | >1.8 | 2.39 |    | 134 |
| 2y | Ado—$N^1$—O | 2-$OCH_3$ | 2.7 | 0.17 | 320 | 1935 |
|    |    |    | >3.1 | 0.11 |    | >3020 |
| 2z | " | 3,4-$CH_3$ | >2.6 | 0.32 | 320 | >1000 |

TABLE 3-continued

Activity vs Vaccinia Virus Substituted-Benzyloxy Derivatives (grouped by substituents)

OCH₂—⟨R⟩

| Compd. | Base | R | $V_r^a$ | $ID_{50}^b$ | $MTC^c$ | $TI^d$ |
|---|---|---|---|---|---|---|
| | | | >2.8 | 0.18 | | >1760 |
| 2aa | " | 3,5-CH₃ | >2.5 | 0.45 | 320 | 710 |
| | | | >2.6 | 0.32 | | >1000 |
| 2bb | " | 2,5-CH₃ | >2.6 | 0.38 | 320 | >850 |
| | | | >2.8 | 0.24 | | >1350 |
| 2cc | " | 2,4-CH₃ | 2.9 | 0.08 | 320 | 4110 |
| | | | 2.9 | 0.08 | | 3890 |
| 2dd | " | —H | >2.0 | 1.77 | 320 | 180 |
| | | | >2.0 | 1.77 | | 180 |
| 2ff | " | 2,6-F | >2.0 | 1.55 | 320 | 205 |
| | | | >2.0 | 1.83 | | 175 |
| 2gg | " | 2,5-F | >2.0 | 1.77 | 320 | 180 |
| | | | >1.9 | 2.79 | | 115 |
| Control | Ara—A | — | 1.0 | 2.00 | >320 | 13.3 |

[a]VR - Virus rating calculated by the method of R. W. Sidwell and J. N. Huffman, Appl. Microbiol., 22, 797–801 (1971).
[b]ID₅₀ - Inhibitory dose 50. Concentration of the drug that causes a 50% reduction in virus replication.
[c]MTC - Minimum toxic concentration. The lowest concentration of the test compound that results in a 50% reduction in the percent survival of viable host cells.
[d]TI - Therapeutic index. A measure of the antiviral potential for the drug calculated as MTC/ID₅₀. TI > 50 indicates a useful compound.

EXAMPLE 30

Activity of Adenosine-N'-Oxides and Substituted 1-(Benzyloxy)adenosines in Vivo The in vivo model used in these studies was originally developed by Boyle et al (Antimicrob. Agents Chemother., 1966, 1967, 536) and further defined by Joshi et al (Appl. Microbiol. 1969, 18, 935). Mice inoculated in the tail vein with vaccinia virus develop dermal lesions over the entire tail surface. These lesions, enumerated after fluorescence staining, are a function of the virus challenge level, animal weight and inoculation distance from the base of the tail. The IHD strain of vaccinia virus, passaged once in mouse brain and once in primary rabbit kidney cell culture, was used. Outbred Swiss mice (CD-1, VAF+, Charles River Laboratories, Inc ), weighing 18–21 g, were inoculated with 0.2 ml of a 1:40 dilution of the stock virus via the tail vein (1 cm from the base). Test compounds were administered intraperitoneally once daily for seven days, with the first dose given the day preceding virus challenge. Each treatment group was composed of 20 virus-infected mice. Uninfected, drug-treated toxicity controls (5 mice per group) were included for each treatment administered. The positive control compound, which was included in all assays, was ara-A. Diluent control mice received inoculations with the appropriate compound diluent on the same schedule as the compound treated mice. Animals were sacrificed on the sixth day and their tails were stained with a solution of 1% fluorescein-0.5% methylene blue in 70% methanol. Lesions were enumerated under UV light (254 nm) with the aid of a hand lens. The mean and medium number of lesions for each treatment group were calculated prior to, and following square root transformation of the individual tailpox counts. Tailpox counts from each of the treatment groups were compared by Student's t test.

Comparison of test compounds with untreated controls is shown in Table 4. A greater figure for $$\left[1 - \frac{\text{Treated pox}}{\text{Control pox}}\right] \times 100$$

indicates greater antiviral activity.

TABLE 4

In Vivo Activity vs. Vaccinia Virus Mouse Tail Pox Model (IP Drug)

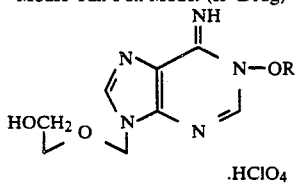

.HClO₄

| Compound | R | $\left[1 - \frac{\text{Treated pox}}{\text{Control pox}}\right](100)$ |
|---|---|---|
| 2c | 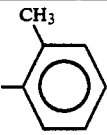 CH₃ | 50 |
| 2i | 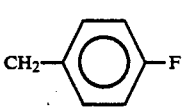 F | 31 |
| 2aa |  CH₃, CH₃ | 57 |

TABLE 4-continued

In Vivo Activity vs. Vaccinia Virus
Mouse Tail Pox Model (IP Drug)

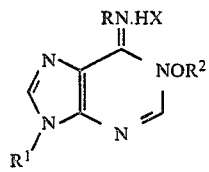

| Compound | R | $\left[1 - \dfrac{\text{Treated pox}}{\text{Control pox}}\right](100)$ |
|---|---|---|
| 2b | 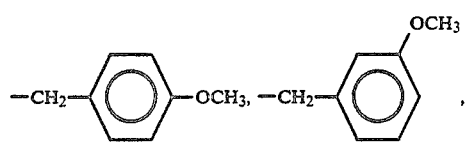 (–CH₂–C₆H₄–CH₃, para) | 39 |
| 2a | (–CH₂–C₆H₄–CH₃, meta) | 54 |
| 21 | (–CH₂–C₆H₄–CF₃) | 39 |
| — | AraA | 53 |
| 1a | Parent N-oxide | 44 |

What is claimed is:

1. A compound of the formula

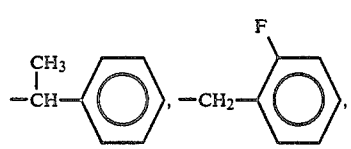

where

X is perchlorate, hydrogen or fluoroborate,
R is hydrogen or methyl
$R^1$ is ribosyl or 2'-deoxyribosyl, and
$R^2$ is a member selected from the group consisting of the following substituted arylalkyl groups:

$-CH_2-C_6H_4-OCH_3$, $-CH_2-C_6H_4-OCH_3$, $-CH(CH_3)-C_6H_5$, $-CH_2-C_6H_4-F$,

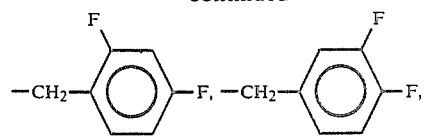

$-CH_2-C_6H_3F_2$, $-CH_2-C_6H_3F_2$,

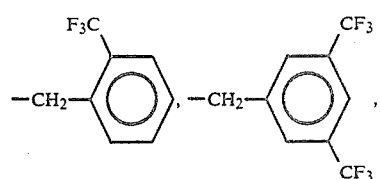

$-CH_2-C_6H_4-CF_3$, $-CH_2-C_6H_3(CF_3)_2$,

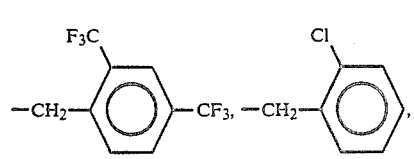

$-CH_2-C_6H_3(CF_3)_2$, $-CH_2-C_6H_4-Cl$,

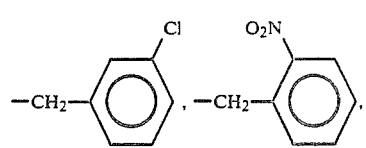

$-CH_2-C_6H_4-Cl$, $-CH_2-C_6H_4-NO_2$,

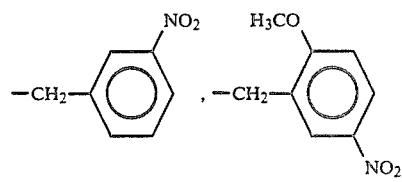

$-CH_2-C_6H_4-NO_2$, $-CH_2-C_6H_3(OCH_3)(NO_2)$,

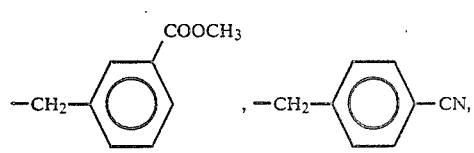

$-CH_2-C_6H_4-COOCH_3$, $-CH_2-C_6H_4-CN$,

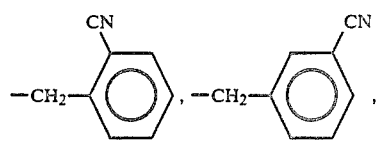

$-CH_2-C_6H_4-CN$, $-CH_2-C_6H_4-CN$,

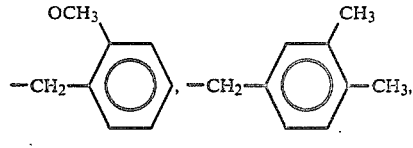

$-CH_2-C_6H_4-OCH_3$, $-CH_2-C_6H_3(CH_3)_2$,

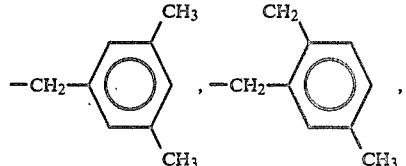

$-CH_2-C_6H_3(CH_3)_2$, $-CH_2-C_6H_3(CH_3)_2$,

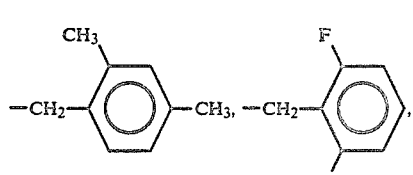

$-CH_2-C_6H_3(CH_3)_2$, $-CH_2-C_6H_3F_2$,

-continued

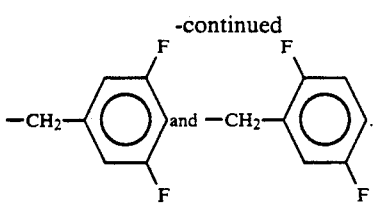

2. The compound of claim 1 wherein $R^1$ is ribosyl.
3. The compound of claim 1 wherein X is perchlorate.
4. The compound of claim 1 wherein R is hydrogen.
5. The compound of claim 1 that is 1-(4-methoxybenzyloxy)adenosine, perchloric acid salt.
6. The compound of claim 1 that is 1-(3-methoxybenzyloxy)adenosine, perchloric acid salt.
7. The compound of claim 1 that is 1-(1-phenylethyloxy)adenosine, perchloric acid salt.
8. The compound of claim 1 that is 1-(2-fluorobenzyloxy)adenosine, perchloric acid salt.
9. The compound of claim 1 that is 1-(2,4-difluorobenzyloxy)adenosine, perchloric acid salt.
10. The compound of claim 1 that is 1-(3,4-difluorobenzyloxy)adenosine, perchloric acid salt.
11. The compound of claim 1 that is 1-(2-trifluoromethylbenzyloxy)adenosine, perchloric acid salt.
12. The compound of claim 1 that is 1-[3,5-bis(trifluoromethyl)benzyloxy]adenosine, perchloric acid salt.
13. The compound of claim 1 that is 1-[2,4-bis(trifluoromethyl)benzyloxy]adenosine, perchloric acid salt.
14. The compound of claim 1 that is 1-(2-chlorobenzyloxy)adenosine, perchloric acid salt.
15. The compound of claim 1 that is 1-(3-chlorobenzyloxy)adenosine, perchloric acid salt.
16. The compound of claim 1 that is 1-(2-nitrobenzyloxy)adenosine, perchloric acid salt.
17. The compound of claim 1 that is 1-(3-nitrobenzyloxy)adenosine, perchloric acid salt.
18. The compound of claim 1 that is 1-(2-methoxy-5-nitrobenzyloxy)adenosine, perchloric acid salt.
19. The compound of claim 1 that is 1-(3-methoxycarbonylbenzyloxy)adenosine, perchloric acid salt.
20. The compound of claim 1 that is 1-(4-cyanobenzyloxy)adenosine, perchloric acid salt.
21. The compound of claim 1 that is 1-(2-cyanobenzyloxy)adenosine, perchloric acid salt.
22. The compound of claim 1 that is 1-(3-cyanobenzyloxy)adenosine, perchloric acid salt.
23. The compound of claim 1 that is 1-(2-methoxybenzyloxy)adenosine, perchloric acid salt.
24. The compound of claim 1 that is 1-(3,4-dimethylbenzyloxy)adenosine, perchloric acid salt.
25. The compound of claim 1 that is 1-(3,5-dimethylbenzyloxy)adenosine, perchloric acid salt.
26. The compound of claim 1 that is 1-(2,5-dimethylbenzyloxy)adenosine, perchloric acid salt.
27. The compound of claim 1 that is 1-(2,4-dimethylbenzyloxy)adenosine, perchloric acid salt.
28. The compound of claim 1 that is 1-benzyloxyadenosine, perchloric acid salt.
29. The compound of claim 1 that is 1-(2,6-difluorobenzyloxy)adenosine, perchloric acid salt.
30. The compound of claim 1 that is 1-(3,5-difluorobenzyloxy)adenosine, perchloric acid salt.
31. The compound of claim 1 that is 1-(2,5-difluorobenzyloxy)adenosine, perchloric acid salt.
32. A pharmaceutical composition comprising a compound of claim 1 together with a pharmaceutically acceptable carrier for oral, topical or parenteral administration to mamal.
33. A method for preventing vaccinia viral infection in an animal receiving an administration of a vaccinia virus used as a vector, which method comprises administering to an animal in need thereof a prophylactically effective amount of a compound of claim 1.
34. A method for preventing vaccinia viral infection in an animal receiving an administration of a vaccinia virus used as a vector, which method comprises administering to an animal in need thereof a prophylactically effective amount of a compound of claim 2.
35. A method for preventing vaccinia viral infection in an animal receiving an administration of a vaccinia virus used as a vector, which method comprises administering to an animal in need thereof a prophylactically effective amount of a compound of claim 3.
36. A method for preventing vaccinia viral infection in an animal receiving an administration of a vaccinia virus used as a vector, which method comprises administering to an animal in need thereof a prophylactically effective amount of a compound of claim 4.
37. A method for preventing vaccinia viral infection in an animal receiving an administration of a vaccinia virus used as a vector, which method comprises administering to an animal in need thereof a prophylactically effective amount of a compound selected from the group of the following adenosine $N^1$ oxides and substituted 1-(benzyloxy) adenosines:

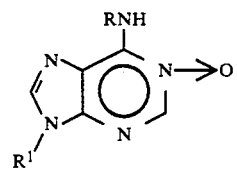

where R is hydrogen or methyl, and $R^1$ is ribosyl or 2'-deoxyribosyl, and

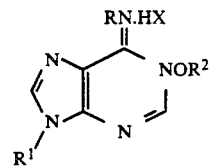

where X, R, $R^1$, and $R^2$ are as defined in claim 1.

38. A method for the treatment of a host animal having a vaccinia virus infection which comprises administering to said host animal a therapeutically effective amount of a compound selected from the group of the following adenosine $N^1$ oxides and substituted 1-(benzyloxy) adenosines:

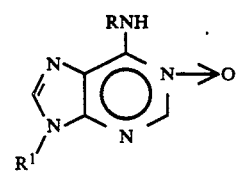

where R is hydrogen or methyl, and $R^1$ is ribosyl or 2'-deoxyribosyl, and

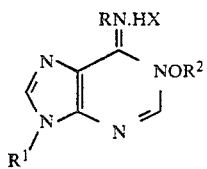

where X, R, R¹, and R² are as defined in claim 1.

39. A method for the treatment of a host animal having a vaccinia virus infection which comprises administering to said host animal a therapeutically effective amount of a compound of the formula

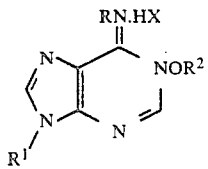

where
X is perchlorate, hydrogen, or fluoroborate,
R is hydrogen or methyl
R¹ is ribosyl or 2'-deoxyribosyl, and
R² is a member selected from the group consisting of the following substituted arylalkyl groups:

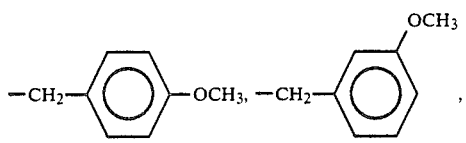

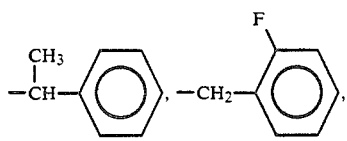

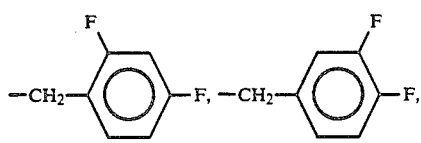

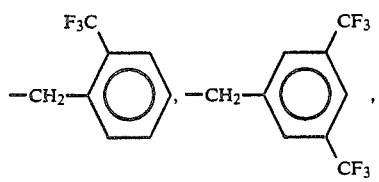

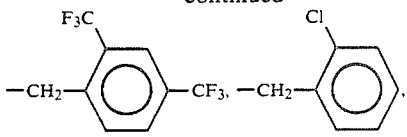

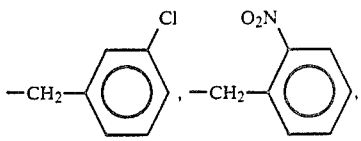

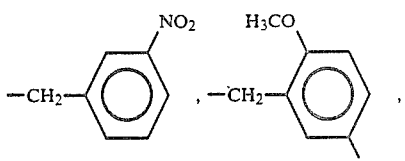

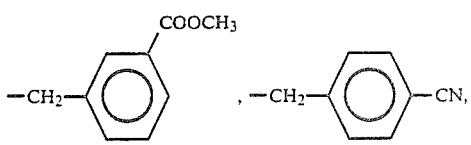

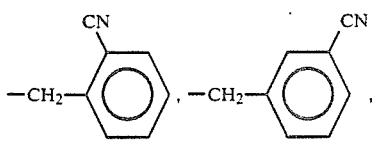

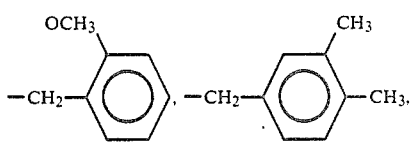

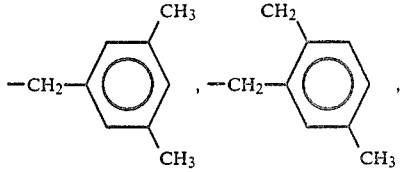

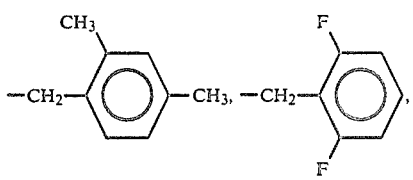

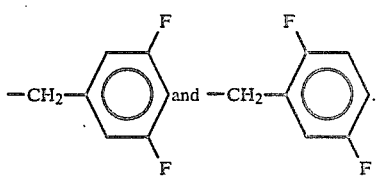

40. The method of claim 39 wherein R¹ is ribosyl.
41. The method of claim 39 wherein X is perchlorate.
42. The method of claim 39 wherein H is hydrogen.